United States Patent
Rimini et al.

(10) Patent No.: US 12,158,541 B2
(45) Date of Patent: Dec. 3, 2024

(54) WIRELESS COMMUNICATION WITH ENHANCED MAXIMUM PERMISSIBLE EXPOSURE (MPE) COMPLIANCE BASED ON VITAL SIGNS DETECTION

(71) Applicant: QUALCOMM Incorporated, San Diego, CA (US)

(72) Inventors: Roberto Rimini, San Diego, CA (US); Tsai-Chen Huang, Mountain View, CA (US); Nitin Jonathan Myers, Austin, TX (US)

(73) Assignee: QUALCOMM Incorporated, San Diego, CA (US)

( * ) Notice: Subject to any disclaimer, the term of this patent is extended or adjusted under 35 U.S.C. 154(b) by 0 days.

(21) Appl. No.: 17/000,228

(22) Filed: Aug. 21, 2020

(65) Prior Publication Data
US 2021/0055386 A1 Feb. 25, 2021

Related U.S. Application Data

(63) Continuation-in-part of application No. 16/548,722, filed on Aug. 22, 2019.
(Continued)

(51) Int. Cl.
*G06F 16/58* (2019.01)
*A61B 5/00* (2006.01)
(Continued)

(52) U.S. Cl.
CPC ............ *G01S 7/415* (2013.01); *A61B 5/0002* (2013.01); *A61B 5/0205* (2013.01);
(Continued)

(58) Field of Classification Search
CPC .......... G01S 7/415; G01S 7/006; G01S 7/354; G01S 13/34; G01S 13/584; G01S 7/4817;
(Continued)

(56) References Cited

U.S. PATENT DOCUMENTS 5,731,778 A * 3/1998 Nakatani ............... G01S 13/584
342/70
6,147,638 A 11/2000 Rohling et al.
(Continued)

FOREIGN PATENT DOCUMENTS

| CN | 102088903 A | 6/2011 |
|----|-------------|--------|
| CN | 102565780 A | 7/2012 |

(Continued)

OTHER PUBLICATIONS

Akdeniz et al., "Millimeter Wave Channel Modeling and Cellular Capacity Evaluation", IEEE JSAC, vol. 32, No. 6, Jun. 2014, pp. 1164-1179 Akdeniz_0614.pdf.
(Continued)

*Primary Examiner* — Tuan A Vu
(74) *Attorney, Agent, or Firm* — Paul M. McAdams; Shumaker & Sieffert, PA

(57) ABSTRACT

Aspects of the disclosure relate to radar-based signaling for detecting, measuring, and/or characterizing a target object. An electronic device may transmit a plurality of detection signals and receive a plurality of reflection signals reflected from the target object. The electronic device then processes the plurality of reflection signals to extract one or more parameters of the target object. Based on the reflection signals, the device can measure and/or characterize the target object, e.g., to obtain a heart rate and/or breathing rate. In other examples, the device may determine whether the reflection signals indicate human vital signs, such as a heart rate or breathing. The electronic device may then adjust at least one transmission parameter based on whether human vital signs are detected at the target object, and transmit the adjusted signal using the transmission parameter. Other aspects, embodiments, and features are also claimed and described.

28 Claims, 8 Drawing Sheets

Related U.S. Application Data

(60) Provisional application No. 62/890,514, filed on Aug. 22, 2019.

(51) Int. Cl.

| | | |
|---|---|---|
| *A61B 5/0205* | (2006.01) | |
| *A61B 5/0507* | (2021.01) | |
| *G01S 7/00* | (2006.01) | |
| *G01S 7/35* | (2006.01) | |
| *G01S 7/41* | (2006.01) | |
| *G01S 13/34* | (2006.01) | |
| *H04W 52/30* | (2009.01) | |
| *A61B 5/024* | (2006.01) | |
| *A61B 5/08* | (2006.01) | |
| *G06F 16/583* | (2019.01) | |

(52) U.S. Cl.
CPC .......... *A61B 5/0507* (2013.01); *A61B 5/4809* (2013.01); *G01S 7/006* (2013.01); *G01S 7/354* (2013.01); *G01S 13/34* (2013.01); *H04W 52/30* (2013.01); *A61B 5/024* (2013.01); *A61B 5/0816* (2013.01); *G06F 16/5854* (2019.01)

(58) Field of Classification Search
CPC .... G01S 13/345; G01S 13/931; G01S 13/522; G01S 5/021; A61B 5/0002; A61B 5/0205; A61B 5/024; A61B 5/0507; A61B 5/0816; A61B 5/4809; A61B 5/1102; A61B 5/05; H04W 52/30; H04W 16/28; H04W 52/0245; H04B 1/3838; H01Q 15/148; G06K 9/2036; H04L 25/4902; H04L 27/362
See application file for complete search history.

(56) References Cited

U.S. PATENT DOCUMENTS

| | | | |
|---|---|---|---|
| 8,398,558 B2 | 3/2013 | Thijs et al. | |
| 9,110,152 B2 | 8/2015 | Ando et al. | |
| 9,515,378 B2 | 12/2016 | Prasad | |
| 9,766,324 B2 | 9/2017 | Katz et al. | |
| 9,915,726 B2 | 3/2018 | Bailey et al. | |
| 10,812,125 B1 | 10/2020 | Badic et al. | |
| 11,169,251 B2 | 11/2021 | Sahin et al. | |
| 2003/0064761 A1* | 4/2003 | Nevermann | H04B 1/3838 455/572 |
| 2005/0156110 A1 | 7/2005 | Crawely | |
| 2006/0208169 A1 | 9/2006 | Breed et al. | |
| 2008/0272956 A1* | 11/2008 | Pedersen | G01S 13/584 342/107 |
| 2011/0144573 A1 | 6/2011 | Rofougaran et al. | |
| 2012/0112955 A1* | 5/2012 | Ando | G01S 13/931 342/159 |
| 2012/0113431 A1 | 5/2012 | Fukuma et al. | |
| 2013/0106657 A1* | 5/2013 | Perthold | G01S 5/021 342/387 |
| 2013/0157729 A1* | 6/2013 | Tabe | H04W 52/0245 455/573 |
| 2014/0118186 A1* | 5/2014 | Nakanishi | G01S 13/345 342/128 |
| 2014/0340569 A1 | 11/2014 | Raskar et al. | |
| 2015/0127343 A1 | 5/2015 | Mullor et al. | |
| 2015/0133173 A1 | 5/2015 | Edge et al. | |
| 2015/0182162 A1 | 7/2015 | Zhao | |
| 2015/0378008 A1* | 12/2015 | Ookawa | G01S 13/931 342/194 |
| 2016/0006914 A1* | 1/2016 | Neumann | G01S 7/4817 348/78 |
| 2016/0327634 A1* | 11/2016 | Katz | H04B 1/3838 |
| 2016/0351996 A1 | 12/2016 | Ou | |
| 2017/0042432 A1* | 2/2017 | Adib | G01S 13/536 |
| 2017/0059688 A1 | 3/2017 | Gan | |
| 2017/0082741 A1* | 3/2017 | Adib | G01S 7/415 |
| 2017/0102457 A1 | 4/2017 | Li et al. | |
| 2017/0127398 A1* | 5/2017 | Andgart | H04W 16/28 |
| 2017/0172425 A1* | 6/2017 | Liu | A61B 5/05 |
| 2017/0311901 A1* | 11/2017 | Zhao | A61B 5/1102 |
| 2018/0059248 A1 | 3/2018 | O'Keeffe | |
| 2018/0103485 A1 | 4/2018 | Jiang et al. | |
| 2018/0287651 A1 | 10/2018 | Fernando et al. | |
| 2018/0372874 A1 | 12/2018 | Lipson et al. | |
| 2019/0007256 A1* | 1/2019 | Chen | H04L 27/362 |
| 2019/0011549 A1 | 1/2019 | Mercuri et al. | |
| 2019/0123442 A1 | 4/2019 | Vannucci et al. | |
| 2019/0166030 A1* | 5/2019 | Chen | H04L 25/4902 |
| 2019/0175074 A1 | 6/2019 | Zhang et al. | |
| 2019/0178985 A1 | 6/2019 | Roh | |
| 2020/0028262 A1* | 1/2020 | Fang | H01Q 15/148 |
| 2020/0081093 A1 | 3/2020 | Rimini et al. | |
| 2020/0134344 A1* | 4/2020 | Joshi | G06K 9/2036 |
| 2021/0055385 A1 | 2/2021 | Rimini | |
| 2022/0260676 A1 | 8/2022 | Rimini et al. | |

FOREIGN PATENT DOCUMENTS

| | | |
|---|---|---|
| CN | 106659428 A | 5/2017 |
| CN | 107636893 A | 1/2018 |
| CN | 108153410 A | 6/2018 |
| CN | 109171688 A | 1/2019 |
| CN | 109924960 A | 6/2019 |
| CN | 110058220 A | 7/2019 |
| EP | 2303121 A1 | 4/2011 |
| EP | 3154153 A1 | 4/2017 |
| TW | 201836287 A | 10/2018 |
| TW | 201838352 A | 10/2018 |

OTHER PUBLICATIONS

Anitori L., et al., "FMCW Radar for Life-sign Detection," IEEE National Radar Conference, May 4-8, 2009, Proceedings., pp. 1-6, 10.1109/RADAR.2009.4976934.

International Search Report and Written Opinion—PCT/US2019/048723—ISA/EPO—Apr. 7, 2020.

Rangan S., et al., "Millimeter-Wave Cellular Wireless Networks: Potentials and Challenges", Proceedings of the IEEE, Mar. 2014, vol. 102, Issue 3, pp. 366-385.

Partial International Search Report—PCT/US2020/047550—ISA/EPO—Sep. 25, 2020.

International Search Report and Written Opinion—PCT/US2020/047550—ISA/EPO—Nov. 18, 2020.

Taiwan Search Report—TW108131289—Feb. 24, 2023, 1 Page.

* cited by examiner

WIRELESS COMMUNICATION WITH ENHANCED MAXIMUM PERMISSIBLE EXPOSURE (MPE) COMPLIANCE BASED ON VITAL SIGNS DETECTION

CLAIM OF PRIORITY UNDER 35 U.S.C. § 119(e)

This application claims priority to and the benefit of provisional patent application No. 62/890,514, filed in the United States Patent and Trademark Office on Aug. 22, 2019, the entire content of which is incorporated herein by reference as if fully set forth below in its entirety and for all applicable purposes.

CLAIM OF PRIORITY UNDER 35 U.S.C. § 120

This application is a continuation-in-part that claims priority to and the benefit of nonprovisional patent application Ser. No. 16/548,722, filed in the United States Patent and Trademark Office on Aug. 22, 2019, the entire content of which is incorporated herein by reference as if fully set forth below in its entirety and for all applicable purposes.

TECHNICAL FIELD

The technology discussed below relates generally to wireless communication and/or vital signs detection systems, and more particularly, to vital signs detection, characterization, and/or measurement using radar-based signaling. Embodiments can provide and enable techniques for detecting and/or measuring vital signs of nearby subjects and/or target objects (e.g., those detected by a wireless proximity sensor or other communication-enabling components) and, in some examples, controlling for maximum permissible exposure.

Introduction

Next-generation wireless telecommunication systems (e.g., such as Fifth Generation (5G) or New Radio (NR) technologies) are being deployed utilizing millimeter-wave (mmW) signals. These signals can operate, for example, at a 28 GHz and 39 GHz spectrum. Although higher frequency signals provide larger bandwidths to efficiently communicate vast amounts of information/data, mmW signals may suffer from high path loss (e.g., path attenuation). To compensate for path loss, transmit power levels can be increased, or beamforming can concentrate energy in a particular direction.

As with various types of electronic signal transmissions, there are usually regulatory rules governing transmission strengths. For example, for mmW signals, the US Federal Communications Commission (FCC) and other regulatory bodies set stringent RF exposure requirements. These rules ensure that the maximum permissible exposure (MPE) on human skin does not exceed a power density of 1 mW/cm$^2$. To meet targeted guidelines, electronic devices are responsible for balancing performance with transmission power and other constraints. This balancing act can be challenging to achieve, especially with devices that have cost, size, and other concerns.

BRIEF SUMMARY OF SOME EXAMPLES

The following presents a simplified summary of one or more aspects of the present disclosure, in order to provide a basic understanding of such aspects. This summary is not an extensive overview of all contemplated features of the disclosure, and is intended neither to identify key or critical elements of all aspects of the disclosure nor to delineate the scope of any or all aspects of the disclosure. Its sole purpose is to present some concepts of one or more aspects of the disclosure in a simplified form as a prelude to the more detailed description that is presented later.

According to some aspects, wireless communication devices, methods, and systems are provided to enable MPE compliance and/or vital sign awareness and detection. For example, a device embodiment (e.g. a mobile apparatus) may include a wireless communication enabling component (e.g., an mmW signal interface). A wireless communication enabling component (e.g., a transceiver) can not only facilitate wireless communication via receipt and transfer of radio frequency signals (e.g., mmW signals), a transceiver can also leverage mmW signaling to detect objects (e.g., objects or subjects nearby or otherwise positioned away from a device embodiment). A device embodiment can utilize object detection features to determine whether objects exhibit human vital signs, such as a heart rate or breathing. If objects are determined to be human, non-human, animate, inanimate, etc., the device can adjust operating parameters of a communication interface (e.g., a mmW transceiver) for MPE compliance (e.g., power up or power down signal transmissions). According to some aspects, signal transmission power adjustments can occur in real time or according to a variety of desired timing arrangements.

In some aspects, the disclosure provides a method, an apparatus, and a computer-readable medium storing computer-executable code for detecting vital signs of a target object. For example, an apparatus may transmit a plurality of detection signals and receive a plurality of reflection signals reflected from the target object. The apparatus may then process the plurality of reflection signals to extract one or more parameters for determining whether the plurality of reflection signals indicate human vital signs. Based on whether human vital signs are detected at the target object, the apparatus may adjust at least one transmission parameter and transmit an adjusted signal using the transmission parameter.

In further aspects, the disclosure provides a method, an apparatus, and a computer-readable medium storing computer-executable code for detecting or measuring vital signs of a target object. For example, an apparatus may obtain a beat signal corresponding to a frequency-modulated continuous wave (FMCW) radar-based reflection signal reflected from the target object, corresponding to a sampling rate. Based on a peak power of a frequency-domain representation of the beat signal, the apparatus may determine a distance to the target object. The apparatus may further determine phase data corresponding to the peak power of the frequency-domain representation of the beat signal, and determine a frequency-domain representation of the phase data based on the sampling rate. Based on the frequency-domain representation of the phase data, the apparatus may then determine the vital signs of the target object.

These and other aspects of the invention will become more fully understood upon a review of the detailed description, which follows. Other aspects, features, and embodiments will become apparent to those of ordinary skill in the art, upon reviewing the following description of specific, exemplary embodiments in conjunction with the accompanying figures. While the following description may discuss various advantages and features relative to certain embodiments and figures, all embodiments can include one or more of the advantageous features discussed herein. In other words, while this description may discuss one or more embodiments as having certain advantageous features, one or more of such features may also be used in accordance with the various embodiments discussed herein. In similar fashion, while this description may discuss exemplary embodiments as device, system, or method embodiments it should be understood that such exemplary embodiments can be implemented in various devices, systems, and methods.

DETAILED DESCRIPTION

Figure 1:
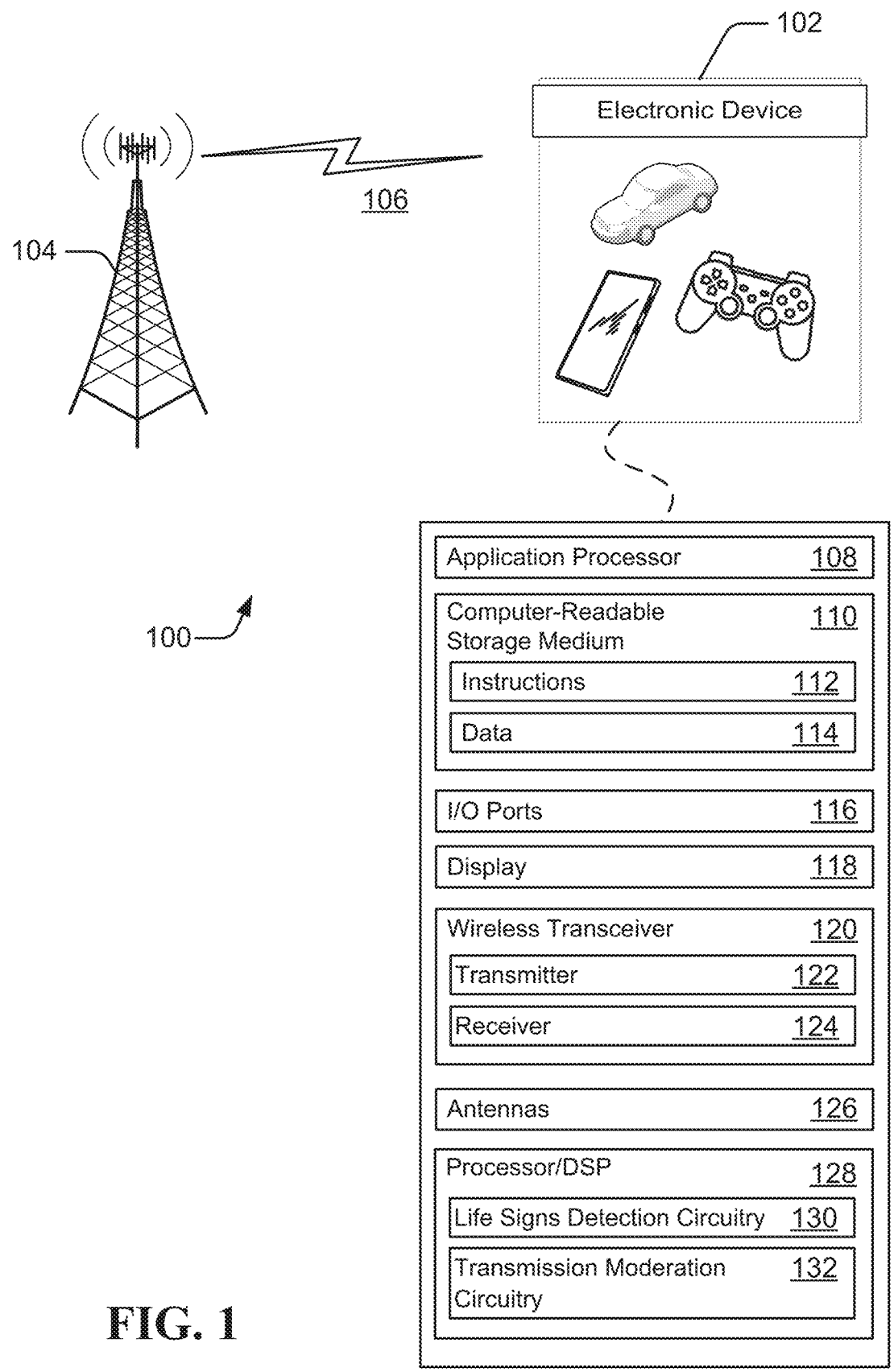
FIG. 1 is a block diagram of a wireless electronic device according to some aspects of the disclosure.

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, those skilled in the art will readily recognize that these concepts may be practiced without these specific details. In some instances, this description provides well known structures and components in block diagram form in order to avoid obscuring such concepts.

While this description describes aspects and embodiments by illustration to some examples, those skilled in the art will understand that additional implementations and use cases may come about in many different arrangements and scenarios. Innovations described herein may be implemented across many differing platform types, devices, systems, shapes, sizes, packaging arrangements. For example, embodiments and/or uses may come about via integrated chip embodiments and other non-module-component based devices (e.g., end-user devices, vehicles, communication devices, computing devices, industrial equipment, retail/purchasing devices, medical devices, AI-enabled devices, etc.). While some examples may or may not be specifically directed to use cases or applications, a wide assortment of applicability of described innovations may occur. Implementations may range a spectrum from chip-level or modular components to non-modular, non-chip-level implementations and further to aggregate, distributed, or OEM devices or systems incorporating one or more aspects of the described innovations. In some practical settings, devices incorporating described aspects and features may also necessarily include additional components and features for implementation and practice of claimed and described embodiments. For example, transmission and reception of wireless signals necessarily includes a number of components for analog and digital purposes (e.g., hardware components including antenna, RF-chains, power amplifiers, modulators, buffer, processor(s), interleaver, adders/summers, etc.). It is intended that innovations described herein may be practiced in a wide variety of devices, chip-level components, systems, distributed arrangements, end-user devices, etc. of varying sizes, shapes and constitution.

An electronic wireless communication device that utilizes millimeter wave (mmW) signals may use a high transmit power to compensate for path loss associated with these signals. A user can physically operate many of these electronic devices, such as a mobile user equipment (UE). Close physical proximity to such an electronic device presents opportunities for radiation to exceed a given guideline, such as a maximum permitted exposure (MPE) limit as determined by the Federal Communications Commission (FCC) or other regulatory body. Because of these issues, it is advantageous to enable devices to moderate one or more transmission parameters, including but not limited to transmit power, based on a proximity of the user.

Some proximity detection techniques may use a dedicated sensor, such as a camera, an infrared (IR) sensor, a radar sensor, etc. to detect a user. However, these sensors may be bulky and expensive. Furthermore, a single electronic device can include multiple antennas positioned on different surfaces (e.g., on a top, a bottom, or opposite sides). To account for each of these antennas, according to some aspects, multiple cameras or sensors may need to be installed near each of these antennas, which further increases a cost and size of the electronic device.

In a further aspect and/or example, the same wireless transceiver utilized for wireless communication can also perform proximity detection. For example, local oscillator (LO) circuitry within a wireless transceiver can generate one or more reference signals that can enable both proximity detection and wireless communication. The LO circuitry can enable the transceiver to transmit a frequency-modulated continuous wave (FMCW) signal or a multi-tone signal for radar-based proximity detection. By analyzing reflections from either of these signals, a UE can determine a range (e.g., distance or slant range) to an object, and in some examples, a material composition of the object.

To ensure compliance with MPE requirements, according to some aspects, a proximity detector, including but not limited to an integrated FMCW-based radar function, can detect the presence of objects and/or nearby targets. Objects may be located around a device, and some objects may be targets of interest. For example, a detector can determine whether a target is within 20 cm of a device's radiating elements. In a further aspect, a device may use detection of multiple objects to create a virtual map of items or subjects having spatial relationships relative to the device. Based on such proximity detection, a device may accordingly adjust one or more transmission parameters used for wireless communication, such as by reducing a transmission power, by switching to a different transmit antenna, etc. And further, based on such proximity detection, a device may accordingly provide proximity information for any other suitable algorithm or scheme, such as home automation functions that may vary based on a user's location. By actively measuring the range to one or more objects, an electronic device can continually monitor its surrounding environment, and can incrementally adjust one or more transmission parameters (or other parameters) to account for the object's movement (e.g., adjustments can increase or decrease transmission power generally or in particular directions via beamformed mmWaves or RF waves).

In general, radar signal processing is tailored to extract a target's location-based information such as its distance, speed, angle, position, etc. However, a typical radar does not provide information about the nature of the target such as whether the target is a living animal/being, human, or not. According to an aspect of the present disclosure, it can be advantageous to adjust one or more transmission parameters used for wireless communication based not only on proximity detection of a nearby target, but in addition, based on a classification of the target. That is, MPE requirements generally only apply to exposure to human beings. If an inanimate object such as a coffee mug or a wall is in close proximity to an electronic device, then MPE requirements may not apply and a high transmission parameter (for example) can continue to be utilized, providing for a more reliable and robust signal. Therefore, including information about objects' spatial locations (e.g., a nearby target or subject location removed from the electronic device), or a classification of the detected proximate target, can help optimize the power transmission of the electronic device.

FIG. 1 illustrates an example electronic device 102 utilizing a radar-based proximity detector according to some aspects of this disclosure. In an example environment 100, the electronic device 102 communicates with a base station 104 through a wireless communication link 106 (wireless link 106). In FIG. 1, the electronic device 102 is illustrated as a smart phone, a vehicle, or a gaming device, to provide some examples. However, an electronic device 102 may be any suitable stationary or mobile apparatus that includes a wireless transceiver. Within the present disclosure, the term electronic device broadly refers to a diverse array of devices and technologies. Electronic devices may include a number of hardware structural components sized, shaped, and arranged to help in communication; such components can include antennas, antenna arrays, RF chains, amplifiers, one or more processors, etc. electrically coupled to each other. For example, some non-limiting examples of a mobile apparatus include a mobile, a cellular (cell) phone, a smart phone, a session initiation protocol (SIP) phone, a laptop, a personal computer (PC), a notebook, a netbook, a smartbook, a tablet, a personal digital assistant (PDA), and a broad array of embedded systems, e.g., corresponding to an "Internet of things" (IoT). A mobile apparatus may additionally be an automotive or other transportation vehicle, a remote sensor or actuator, a robot or robotics device, a satellite radio, a global positioning system (GPS) device, an object tracking device, a drone, a multi-copter, a quad-copter, a remote control device, a consumer and/or wearable device, such as eyewear, a wearable camera, a virtual reality device, a smart watch, a health or fitness tracker, a digital audio player (e.g., MP3 player), a camera, a game console, etc. A mobile apparatus may additionally be a digital home or smart home device such as a home audio, video, and/or multimedia device, an appliance, a vending machine, intelligent lighting, a home security system, a smart meter, augmented reality devices, virtual reality devices, mixed reality devices, etc. A mobile apparatus may additionally be a smart energy device, a security device, a solar panel or solar array, a municipal infrastructure device controlling electric power (e.g., a smart grid), lighting, water, etc.; an industrial automation and enterprise device; a logistics controller; agricultural equipment; military defense equipment, vehicles, aircraft, ships, and weaponry, etc. Still further, a mobile apparatus may provide for connected medicine or telemedicine support, e.g., health care at a distance. Telehealth devices may include telehealth monitoring devices and telehealth administration devices, whose communication may be given preferential treatment or prioritized access over other types of information, e.g., in terms of prioritized access for transport of critical service data, and/or relevant QoS for transport of critical service data. In some examples, the electronic device 102 may be a wireless communication device including a housing shaped and sized to carry one or more components, such as those described below.

In one example, the electronic device 102 may be, or may be a part of, a vehicle that includes a vehicle body configured to carry at least one of a payload or a passenger. In this example, the wireless transceiver 120 may be sized and shaped to be placed in a location proximate to and/or within the vehicle body. In another example, the electronic device 102 may be, or may be a part of, a gaming device that includes a housing sized and shaped to allow a user to participate in an electronic gaming environment. In this example, the wireless transceiver 120 may be sized and shaped to be placed in a location proximate to and/or within the housing. Further, the gaming device may include a visible interface field defining a visual display configured to visually convey object sensing information to the user, and/or one or more user interfaces positioned proximate the housing, for receiving user input, and in response, conveying object sensing information to the user.

The base station 104 communicates with the electronic device 102 via the wireless link 106, which may be implemented as any suitable type of wireless link. Although depicted as a tower of a cellular network, the base station 104 may represent or be implemented as another device, such as a satellite, cable television head-end, terrestrial television broadcast tower, access point, peer-to-peer device, mesh network node, small cell node, fiber optic line, and so forth. Therefore, the electronic device 102 may communicate with the base station 104 or another device via a wired connection, a wireless connection, or a combination thereof.

The wireless link 106 can include a downlink of data or control information communicated from the base station 104 to the electronic device 102 and an uplink of other data or control information communicated from the electronic device 102 to the base station 104. The wireless link 106 may be implemented using any suitable communication protocol or standard, such as 3rd Generation Partnership Project Long-Term Evolution (3GPP LTE), 5th Generation New Radio (5G NR), IEEE 802.11, IEEE 802.16, Bluetooth™, and so forth. In some implementations, instead of or in addition to providing a data link, the wireless link 106 may wirelessly provide power and the base station 104 may include a power source.

The electronic device 102 includes an application processor 108 and a computer-readable storage medium 110 (CRM 110). The application processor 108 may include any type of processor (e.g., an application processor, a digital signal processor (DSP), or a multi-core processor), that executes processor-executable code stored by the CRM 110. The CRM 110 may include any suitable type of data storage media, such as volatile memory (e.g., random access memory (RAM)), non-volatile memory (e.g., Flash memory), optical media, magnetic media (e.g., disk or tape), and so forth. In the context of this disclosure, the CRM 110 is implemented to store instructions 112, data 114, and other information and software of the electronic device 102. The CRM 110 may reside in the application processor 108, external to the application processor 108, or distributed across multiple entities including the application processor 108. The CRM 110 may be embodied in a computer program product. By way of example, a computer program product may include a computer-readable medium in packaging materials. Those skilled in the art will recognize how best to implement the described functionality presented throughout this disclosure depending on the particular application and the overall design constraints imposed on the overall system.

One or more processors 108 may execute software. Software shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise.

The electronic device 102 may also include input/output ports 116 (I/O ports 116) and a display 118. The I/O ports 116 enable data exchanges or interaction with other devices, networks, or users. The I/O ports 116 may include serial ports (e.g., universal serial bus (USB) ports), parallel ports, audio ports, infrared (IR) ports, and so forth. The display 118 presents graphics of the electronic device 102, such as a user interface associated with an operating system, program, or application. Alternately or additionally, the display 118 may be implemented as a display port or virtual interface, through which graphical content of the electronic device 102 is presented.

A wireless transceiver 120 of the electronic device 102 may include a wireless transmitter 122 and a wireless receiver 124. The wireless transceiver 120 provides connectivity to respective networks and other electronic devices connected therewith. In some examples, the wireless transmitter 122 and/or the wireless receiver 124 may be configured for transmitting and/or receiving signals in a millimeter-wave range. Additionally, the electronic device 102 may include a wired transceiver, such as an Ethernet or fiber optic interface for communicating over a local network, intranet, or the Internet. The wireless transceiver 120 may facilitate communication over any suitable type of wireless network, such as a wireless LAN (WLAN), peer-to-peer (P2P) network, mesh network, cellular network, wireless wide-area-network (WWAN), and/or wireless personal-area-network (WPAN). In the context of the example environment 100, the wireless transceiver 120 enables the electronic device 102 to communicate with the base station 104 and networks connected therewith.

The wireless transceiver 120 includes circuitry and logic for transmitting and receiving signals via antennas 126. Components of the wireless transceiver 120 can include amplifiers, mixers, switches, analog-to-digital converters, filters, and so forth for conditioning signals. The wireless transceiver 120 may also include logic to perform in-phase/quadrature (I/Q) operations, such as synthesis, encoding, modulation, decoding, demodulation, and so forth. The wireless transceiver 120 may include one or more components or features for adjusting or controlling transmission parameters. In some cases, components of the wireless transceiver 120 are implemented as separate transmitter 122 and receiver 124 entities. Additionally or alternatively, the wireless transceiver 120 can be realized using multiple or different sections to implement respective transmitting and receiving operations (e.g., separate transmit and receive chains). Although the examples described below generally refer to an integrated wireless transceiver 120 that performs both wireless communication and object sensing operations, aspects of the present disclosure are not limited to this case. For example, the electronic device 102 may include an interface circuit for interfacing with an auxiliary and/or auxiliary sensing device, spaced apart from the housing of the electronic device 102. Auxiliary and/or auxiliary sensing devices can include remote wireless devices capable of communicating with the electronic device 102 (e.g., gaming controller, wearable, augmented/virtual reality device, and other types of mobile devices described above). Here, the interface circuit (not illustrated) can enable communication between the electronic device 102 and the auxiliary sensing device, such that the electronic device 102 receives object-sensing information from the auxiliary sensing device. In response to the object-sensing information, the electronic device 102 may moderate a transmission parameter associated with the wireless transceiver 120 transmitting and/or receiving mmW signals. Moderation of transmission power may include controlling and/or modifying transmission power, such as increasing and/or decreasing or otherwise changing transmission power levels.

The electronic device 102 also includes a processor/digital signal processor (DSP) 128, which is coupled to the wireless transceiver 120. The processor/DSP 128, which may include a modem, can be implemented within or separate from the wireless transceiver 120. Although not explicitly shown, the processor/DSP 128 can include a portion of the CRM 110 or can access the CRM 110 to obtain computer-readable instructions. The processor/DSP 128 controls the wireless transceiver 120 and enables wireless communication or proximity detection to be performed. The processor/DSP 128 can include baseband circuitry to perform high-rate sampling processes that can include analog-to-digital conversion, digital-to-analog conversion, Fourier transforms, gain correction, skew correction, frequency translation, and so forth. The processor/DSP 128 can provide communication data to the wireless transceiver 120 for transmission. The processor/DSP 128 can also process a baseband version of a signal obtained from the wireless transceiver 120 to generate data, which can be provided to other parts of the electronic device 102 via a communication interface for wireless communication or proximity detection.

Although not explicitly depicted, the wireless transceiver 120 or the processor/DSP 128 can also include a controller. The controller can include at least one processor and at least one CRM, such as the application processor 108 and the CRM 110. The CRM can store computer-executable instructions, such as the instructions 112. The processor and the CRM can be localized at one module or one integrated circuit chip or can be distributed across multiple modules or chips. Together, a processor and associated instructions can be realized in separate circuitry, fixed logic circuitry, hard-coded logic, and so forth. The controller can be implemented as part of the wireless transceiver 120, the processor/DSP 128, a special-purpose processor configured to perform MPE techniques, a general-purpose processor, some combination thereof, and so forth.

The processor/DSP 128 may include life signs detection circuitry 130 and transmission moderation circuitry 132. As described further below, the life signs detection circuitry 130 may be configured to process reflected signals, e.g., from an FMCW radar, to extract one or more parameters for determining whether the reflected signals indicate human vital signs (e.g., a breathing rate, a heart rate, and/or a condition or data corresponding to human organs) and/or vital signs associated with other types of living animals. For example, the life signs detection circuitry 130 may combine transmitted detection signals with received reflection signals to obtain beat signals corresponding to a given sampling rate. The life signs detection circuitry 130 may further determine a received power of the beat signals as a function of frequency, and determine phase data corresponding to a peak power (as a function of frequency) of each one of the beat signals. The life signs detection circuitry 130 may further determine a frequency-domain representation of the phase data with respect to the sampling rate. Thus, in some examples, the life signs detection circuitry 130 may determine a heart rate, a breathing rate, and/or a sleep pattern based on the phase data. In some examples, the life signs detection circuitry 130 may detect an indication of human vital signs by determining whether the frequency-domain representation of the phase data includes a peak within a frequency range corresponding to the human vital signs. In some examples, the life signs detection circuitry 130 may apply a high-pass filter to the phase data to attenuate a lower-frequency signal associated with breathing, for enhancing a higher-frequency signal associated with a heart rate. In still further examples, the life signs detection circuitry 130 may calculate a difference between values of the frequency-domain representation of the phase data in consecutive samples, and detect an indication of human vital signs by determining whether the difference includes a peak within a frequency range corresponding to the human vital signs. And in still further examples, the life signs detection circuitry 130 may utilize a multiple signal classification (MUSIC) or estimation of signal parameters using rotational invariance (ESPRIT) for spectral estimation of the phase data. The transmission moderation circuitry 132 may control one or more transmission parameters corresponding to the wireless transceiver 120 based on whether or not a detected target object is human and/or corresponds to a living animal of interest. For example, the transmission moderation circuitry 132 may control the wireless transceiver 120 to adjust at least one of a power level of an uplink signal, a beam steering angle of the uplink signal, a frequency of the uplink signal, a selected antenna of the uplink signal, a communication protocol of the uplink signal, or a combination of the above, such that the power of the uplink signal at the human target object is no greater than the MPE regulatory requirements.

Figure 2:
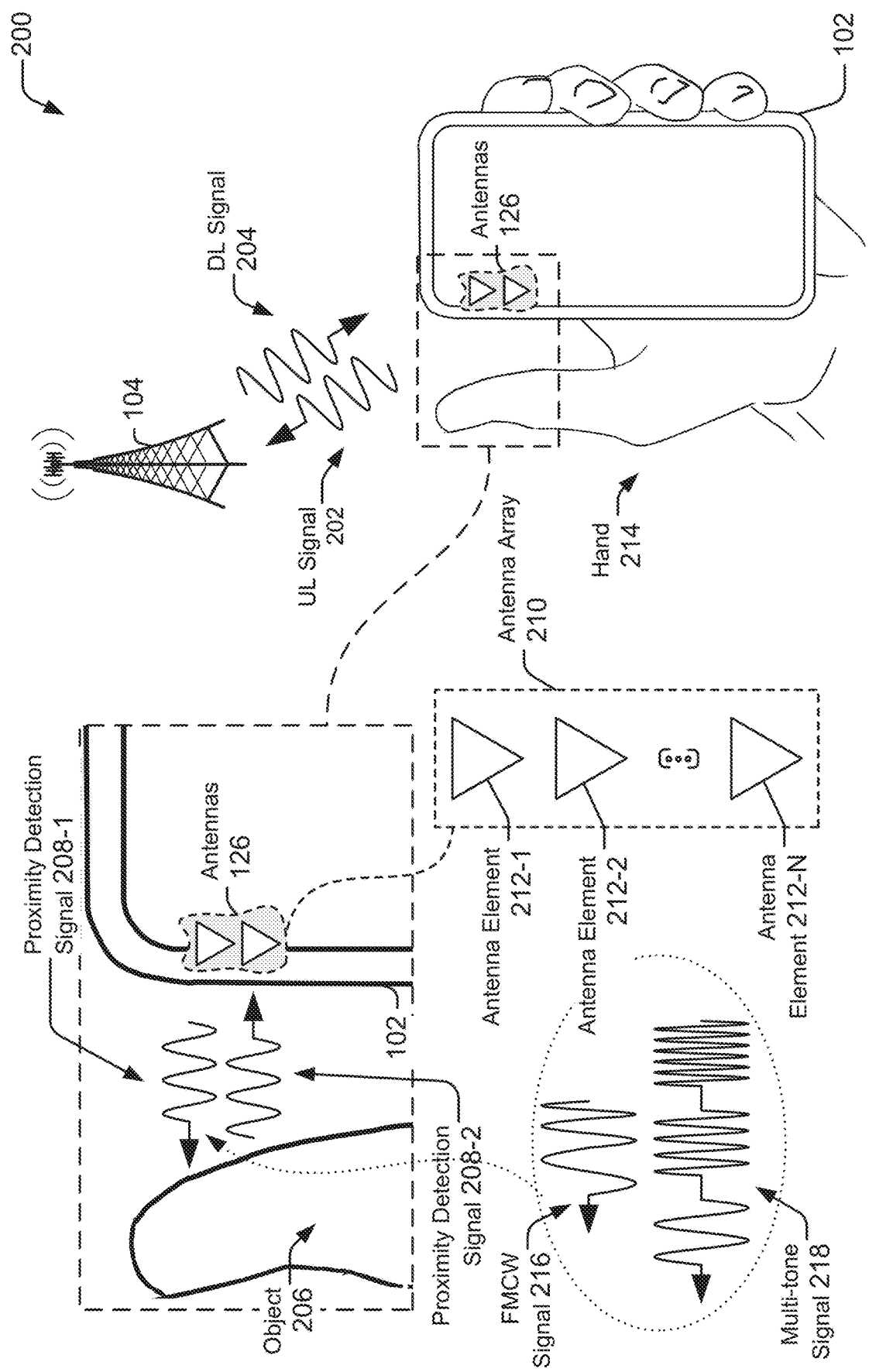
FIG. 2 is a schematic diagram of an operating environment for an electronic device utilizing a radar-based proximity detector according to some aspects of the disclosure.

FIG. 2 illustrates an example operating environment 200 for detecting and characterizing target objects utilizing a radar-based proximity detector. In the example environment 200, a hand 214 of a user holds the electronic device 102. In one aspect, the electronic device 102 communicates with the base station 104 by transmitting an uplink signal 202 (UL signal 202) or receiving a downlink signal 204 (DL signal 204) via at least one of the antennas 126. A user's thumb, however, may represent a proximate target object 206 that may be exposed to radiation via the uplink signal 202. To determine a range to the target object 206, the electronic device 102 transmits a proximity detection signal 208-1 via at least one of the antennas 126 and receives a reflected proximity detection signal 208-2 via at least another one of the antennas 126.

In one implementation, the proximity detection signal 208-1 includes a frequency-modulated continuous-wave (FMCW) signal 216. In general, a frequency of the FMCW signal 216 increases or decreases across a time interval. Different types of frequency modulations may be used, including linear-frequency modulations (LFM) (e.g., chirp), sawtooth-frequency modulations, triangular-frequency modulations, and so forth. The FMCW signal 216 enables radar-based ranging techniques to be utilized to determine the range to the target object 206. To achieve a finer range resolution (e.g., on the order of centimeters (cm)) for close-range applications, larger bandwidths can be utilized, such as 1 gigahertz (GHz), 4 GHz, 8 GHz, and so forth. For instance, the FMCW signal 216 can have a bandwidth of approximately 4 GHz and include frequencies between approximately 26 and 30 GHz. The finer range resolution improves range accuracy and enables multiple objects 206 to be distinguished in range. The FMCW signal 216 can provide an accurate range measurement for a variety of distances based on the bandwidth (e.g., between approximately 4 and 20 cm for a 4 GHz bandwidth). An amount of time for performing proximity detection can also be relatively short using the FMCW signal 216, such as within approximately one microsecond.

In another implementation, the proximity detection signal 208 may be a multi-tone signal 218, which includes at least three tones (e.g., frequencies). The multi-tone signal 218 can be generated using existing components within the wireless transceiver 120, which are also used to generate the uplink signal 202. For example, the multi-tone signal 218 can be generated using an existing phase lock loop (PLL), using Orthogonal Frequency-Division Multiplexing (OFDM), or using a multi-tone transmit signal generated at baseband via a digital signal generator. Depending on the technique used, an amount of time for performing proximity detection via the multi-tone signal 218 can be on the order of approximately one microsecond and 400 microseconds. Frequency separations between the tones can be on the order of megahertz (MHz) or GHz. A bandwidth of the multi-tone signal 218 can be, for example, approximately 800 MHz or 2 GHz. The range to the object 206 is determined by analyzing a change in phase across each of these tones. To improve range accuracy, larger bandwidths (e.g., separations between tones) or larger quantities of tones can be used. The multi-tone signal 218 can be used to measure ranges between approximately 0 and 7 cm.

In some electronic devices 102, the antennas 126 may include at least two different antennas, at least two antenna elements 212 of an antenna array 210, at least two antenna elements 212 associated with different antenna arrays 210, or any combination thereof. As shown in FIG. 2, the antennas 126 correspond to the antenna elements 212 within the antenna array 210, which can include multiple antenna elements 212-1 to 212-N, where N represents a positive integer. Using at least one of the antenna elements 212, the wireless transceiver 120 can transmit the proximity detection signal 208-1 while receiving the reflected proximity detection signal 208-2 using at least another one of the antenna elements 212. In other words, the wireless transceiver 120 can receive the reflected proximity detection signal 208-2 via a first antenna element 212-1 during a portion of time that the proximity detection signal 208-1 is transmitted via a second antenna element 212-2. The antennas 124 and/or elements thereof may be implemented using any type of antenna, including patch antennas, dipole antennas, and so forth.

If the electronic device 102 includes multiple antennas 126 located on different sides of the electronic device 102 (e.g., a top, a bottom, or opposite sides), the described techniques can enable the user to be detected with respect to each antenna 126. In this way, transmission parameters can be independently adjusted relative to the range of the object 206 with respect to each antenna 126. Such independent detection therefore enables the two or more of the antennas 126 to be configured for different purposes. For example, one of the antennas 126 can be configured for enhanced communication performance while another one of the antennas 126 is simultaneously configured to comply with FCC requirements. As described in further detail with respect to FIG. 3, some of the components of the wireless transceiver 120 can be utilized for both wireless communication and proximity detection.

Figure 3:
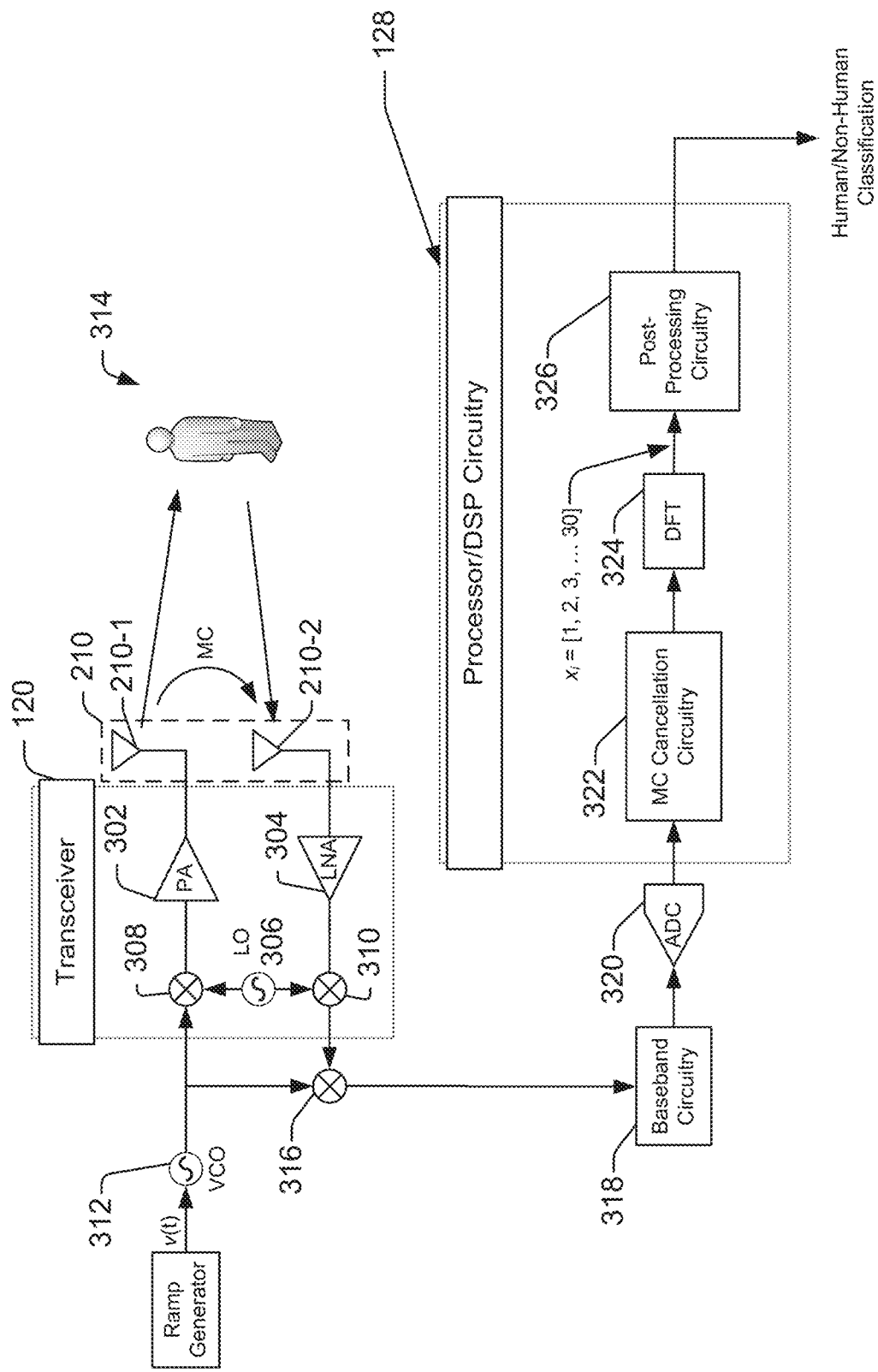
FIG. 3 is a block diagram illustrating additional detail of a portion of an electronic device according to some aspects of the disclosure.

FIG. 3 illustrates an example implementation of a wireless transceiver 120 and processor/DSP circuitry 128 for moderating a transmission to reduce exposure to human target objects according to some aspects of this disclosure. The wireless transceiver 120 may include a transmitter 122 and a receiver 124, which are respectively coupled between the processor/DSP 128 and an antenna array 210. The transceiver 120 includes a power amplifier (PA) 302 configured to amplify a signal for transmission from a transmit antenna 210-1. The transceiver 120 further includes a low-noise amplifier (LNA) 304 for amplifying a signal received by a receive antenna 210-2. Local oscillator (LO) circuitry 306 is coupled to mixers 308 and 310. The LO circuitry 306 generates at least one reference signal, which enables the mixers 308 and 310 to upconvert or downconvert analog signals within the transmit or receive chains, respectively. The LO circuitry 306 may further be configured to generate one or more different types of reference signals to support both target object proximity detection/characterization, and wireless communication. In some examples, the LO circuitry 306 may be configured to generate one or more in-phase and quadrature (I/Q) reference signals. In this manner, the transmission from the transmit antenna 210-1 may include I and Q components. And further, after the reflected signal is received from the receive antenna 210-2, I and Q components of the reflected signal may be separated from one another for processing.

The transceiver 120 can also include other additional components that are not depicted in FIG. 3. These additional components can include band-pass filters, additional mixers, switches, and so forth. Moreover, as discussed above, the transceiver 120 may be configured not only for the target object ranging and detection described immediately below, but additionally for wireless communication.

Although not explicitly depicted, the wireless transceiver 120 and/or the processor/DSP 128 can also include a controller. The controller can include at least one processor and at least one CRM, such as the application processor 108 and the CRM 110. The CRM can store computer-executable instructions, such as the instructions 112. The processor and the CRM can be localized at one module or one integrated circuit chip or can be distributed across multiple modules or chips. Together, a processor and associated instructions can be realized in separate circuitry, fixed logic circuitry, hard-coded logic, and so forth. The controller can be implemented as part of the wireless transceiver 120, the processor/DSP 128, a special-purpose processor configured to perform MPE techniques, a general-purpose processor, some combination thereof, and so forth.

A voltage-controlled oscillator (VCO) 312 may be configured to generate a sinusoidal signal having a frequency that depends on a voltage of an input signal v(t). That is, by properly varying the input signal v(t) to the VCO 312, the VCO 312 may generate, for example, a sinusoid of increasing frequency over time, often called a chirp signal. This chirp signal can be utilized for an FMCW-based radar. Of course, other suitable input signals v(t), and other suitable radar configurations may be utilized within the scope of this disclosure for proximity detection and target object sampling.

The chirp signal may be amplified by the PA 302 and mixed with the LO signal (i.e., upconverted) at the mixer 308 for transmission from a transmit antenna 210-1. The transmitted signal may reflect off a target object 314, being reflected back to a receive antenna 210-2. The reflected signal at the receive antenna 210-2 may be mixed with the LO signal (i.e., downconverted) at the mixer 310 and amplified by the LNA 304.

The output of the LNA 304 (i.e., the amplified received signal) may be mixed with the chirp signal at a mixer 316. With an FMCW-based radar, this mixing creates a beat signal, which is representative of a frequency offset between the radio-frequency transmit signal and the radio-frequency receive signal. In general, the frequency of the beat signal is proportional to the distance of the target object 314.

The beat signal may be processed by baseband circuitry 318, configured to perform various baseband functions including but not limited to gain correction, skew correction, frequency translation, etc. The output from the baseband circuitry 318 may be converted to the digital domain utilizing one or more analog-to-digital converters (ADC) 320. In an example wherein the radar transmission includes I and Q components, as discussed above, the output from the baseband circuitry 318 may include separate I and Q signals, and the ADC 320 may include two ADCs for respectively converting each of the I and Q components to the digital domain. The digital output from the ADC 320 may then be provided to the processor/DSP circuitry 128. In some implementations, the processor/DSP circuitry 128 may be a DSP or any suitable functional component for carrying out the below-described processes.

An undesired side effect of having a closely located transmit antenna 210-1 and receive antenna 210-2, as may occur in a small electronic device, is mutual coupling (MC). That is, part of the transmitted energy may couple back to the receiver. This mutual coupling is a well-known issue in the art. Within the processor/DSP circuitry 128, MC cancellation circuitry 322 may provide cancellation of the undesired energy coupled between the transmit antenna 210-1 and the receive antenna 210-2. To remove the MC component from the received signal, the MC cancellation circuitry 322 uses the transmit signal to cancel the MC component. Although not explicitly shown, the MC cancellation can be performed in a time domain or a frequency domain via the MC cancellation circuitry 322.

After cancelling the MC, discrete Fourier transform (DFT) circuitry 324 may convert the received beat signal to the frequency domain and provide samples of the beat signal in this domain. For example, if 30 measurements of the target object 314 are obtained from 30 sequential target object reflections, the output x from the DFT circuitry 324 includes $x_i = [x_1, x_2, \ldots, x_{30}]$ as its output. Here, each sample $x_i$ corresponds to a spectrum measured from a single radar reflection. These samples $x_i$ may then be sent to post-processing circuitry 326. Post-processing circuitry 326 may then process the samples x to determine, for example, whether the target object 314 may be characterized as human. Further discussion of the classification of the target object 314 as a human, based on detecting human vital signs, is provided below. In another example, post-processing circuitry 326 may process the samples x to determine one or more parameters or characteristics of the target object 314, including, but not limited to a location, motion, a breathing rate, a heart rate, etc.

Based on the categorization of the target object 314, the processor/DSP circuitry 128 can generate a transmission parameter that controls one or more transmission attributes for wireless communication. By specifying the transmission parameter, the processor/DSP circuitry 128 can, for example, cause the transceiver 120 to decrease a transmit power if a target object 314 that is near the electronic device 102 is a human, or increase the transmit power if the target object 314 is farther away from the electronic device 102 and/or is not a human. For example, the power amplifier 302 may be dynamically controlled based on the target object classification. If the target object 314 is determined to not be human, the processor 122 can, for example, keep the transmission parameter unchanged. The transmission parameter can adjust a power level, a beam steering angle, a frequency, a selected antenna or antenna array, or a communication protocol that is used to transmit an uplink signal. The ability to determine the range to the target object 314 and the category of the target object 314, and to control the transceiver 120, enables the processor 122 to balance performance of the electronic device 102 with compliance or radiation requirements.

The processor/DSP circuitry 128 may also be coupled to the LO circuitry 306, which can enable the processor/DSP circuitry 128 to control the LO circuitry 306 via a mode signal. The mode signal, for example, can cause the LO circuitry 306 to switch between generating reference signals for target object detection/classification, or generating reference signals for wireless communication. In other implementations, the application processor 108 (see FIG. 1) can perform one or more of these functions.

Although the wireless transceiver 120 is shown as a direct-conversion transceiver in FIG. 3, the described techniques can also be applied to other types of transceivers, such as superheterodyne transceivers. In general, the LO circuitry 306 can be used to perform frequency conversion between any frequency stage (e.g., between baseband frequencies and radio frequencies, between intermediate frequencies and radio frequencies, or between baseband frequencies and intermediate frequencies).

According to some aspects of this disclosure, an electronic device may exploit certain characteristics known to correspond to a human target object, to determine whether a target object is human. For example, by utilizing a radar-based proximity detection circuit as described above, the electronic device can not only detect the proximity of a target object. But further, the electronic device can detect one or more dynamic parameters associated with the target object, generally relating to movement, time-varying position, etc., of the target object. For example, the electronic device can detect movements indicative of vital signs of a human, other types of living animals, and/or organs for a human or other living animal. As particular examples, the electronic device can detect movements characteristic of breathing and heart rate or pulse.

In an example where the electronic device is facing MPE requirements, the electronic device can accordingly adjust transmission parameters such that a target object's exposure to transmitted radiation is no greater than an MPE requirement if the electronic device detects a human being in its proximity. That is, even if a target object is in close proximity to the electronic device, if the electronic device detects that the target object is not human, namely, does not exhibit human vital signs such as breathing rate and/or pulse rate, then the electronic device may transmit without regard to MPE requirements.

In various examples described further below, vital signs detection may consist of observing multiple successive radar echoes, and extracting dynamic phase changes in the reflected signal. These phase changes provide a sensitive signal that can be compared to known human vital signs to provide a reliable indication whether the detected target object is human.

Figure 4:
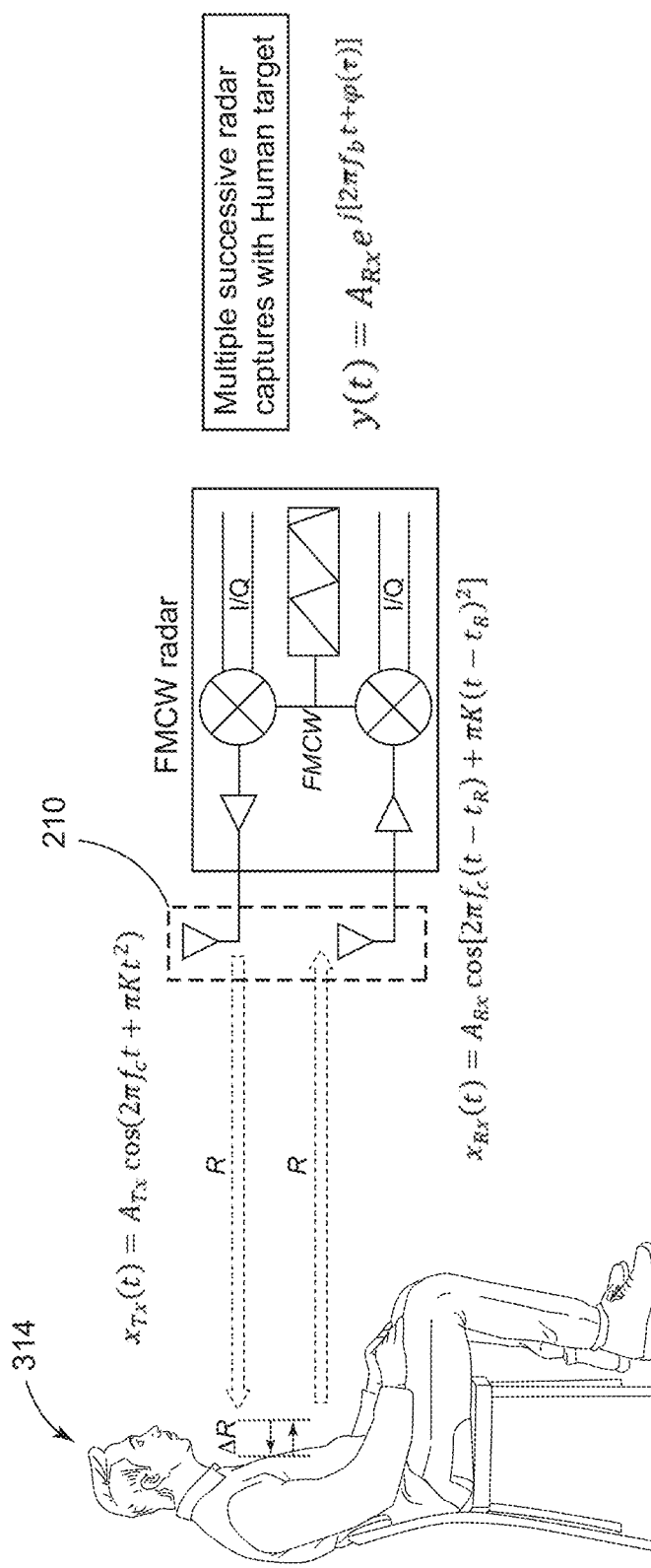
FIG. 4 is a schematic illustration of a radio frequency wave (e.g. a continuous wave, modulated wave, or frequency-modulated continuous wave (FMCW)) radar-based human-vital-signs detection according to some aspects of the disclosure.

FIG. 4 is a schematic illustration showing a portion of an electronic device, including an FMCW radar-based proximity detector, operating in proximity to a person 314 sitting on a chair at a distance R from an antenna element 210. The electronic device transmits a radar pulse $x_{Tx}(t)$ toward the person, who is attempting to sit still. In this example, the FMCW radar transmits the following pulse:

$$x_{Tx} = A_{Tx} \cos(2\pi f_c t + \pi K t^2)$$

Here, $A_{Tx}$ represents the amplitude of the transmitted signal; $f_c$ represents the frequency; t is time; and K is a parameter of the FMCW radar indicating how fast the frequency increases over time. That is, $K = BW/(T_{chirp})$, where BW is the bandwidth of the chirp and $T_{Chirp}$ is the time duration of the chirp.

After reflecting off the person 314, the reflected signal $x_{Rx}(t)$ is received back at the electronic device. In this example, the reflected signal appears as follows:

$$x_{Rx} = A_{Rx} \cos[2\pi f_c(t-t_R) + \pi K(t-t_R)^2]$$

Here, $A_{Rx}$ represents the amplitude of the received signal; $t_R$ represents a time delay. The time delay is proportional to the round trip distance, and takes the value $$t_R = \frac{2R}{c}.$$

As discussed above, the FMCW radar multiplies the transmitted and reflected signals with one another, to obtain a beat signal y(t):

$$y(t) = A_{Rx} e^{j[2\pi f_b t + \varphi(\tau)]}$$

Here, $f_b$ represents the beat frequency, and $\varphi(\tau)$ represents the phase of the beat signal.

The beat frequency $f_b$ contains information about the distance R to the person. That is, the beat frequency $f_b$ is proportional to the distance R according to the equation:

$$f_b = \frac{2KR}{c}$$

Referring to FIG. 4, as illustrated, the radar signal may reflect off the person's chest. As the person breathes and their chest moves in and out, the distance R varies by small amounts, represented as ΔR. Specifically, as illustrated, the travelled distance R reduces due to chest expansion when the person inhales, and increases when the person exhales.

When an electronic device with an FMCW radar determines the distance R to the person, in general, the resolution of such distance measurements may be relatively coarse. If the resolution, or the range-bin width, is larger than the chest displacement ΔR caused by the person's breathing, then even though the distance R is changing over time, the determined value of R may remain the same. However, the inventors have noticed that the beat signal phase φ provides a more sensitive signal that can be utilized to detect small variations in distance, such as those caused by chest displacement when breathing. That is, a generally periodic variation of distance ΔR, corresponding to breathing, also corresponds to a generally periodic variation in the phase φ of the beat signal. This phase variation over time is given by the equation:

$$\varphi(\tau) = \frac{4\pi \Delta R(\tau)}{\lambda}$$

Here, λ represents the wavelength of the FMCW radar signal, and τ represents the time of the measurement. In an example where the wireless communication device operates its FMCW radar in the mmW band, the wavelength λ is generally less than 1 cm, on the order of millimeters.

Accordingly, aspects of the present disclosure exploit the sub-cm wavelength λ of the mmW signal to measure the temporal phase evolution of the reflected signal to estimate the generally periodic phase patterns caused by human vital signs. While the above discussion has focused on variations caused by breathing, this disclosure is not limited to variations caused only by breathing. As discussed in further detail below, at least a person's heart rate can also cause measurable variations in the phase φ of the reflected signal. That is, the pressure variations in the heart due to a systole and a diastole is generally periodic, with the heart beat rate as its frequency. This generally periodic pressure variation results in a generally periodic micro-vibration of a person's skin, which can be detected utilizing the measurements described herein.

Figure 5:
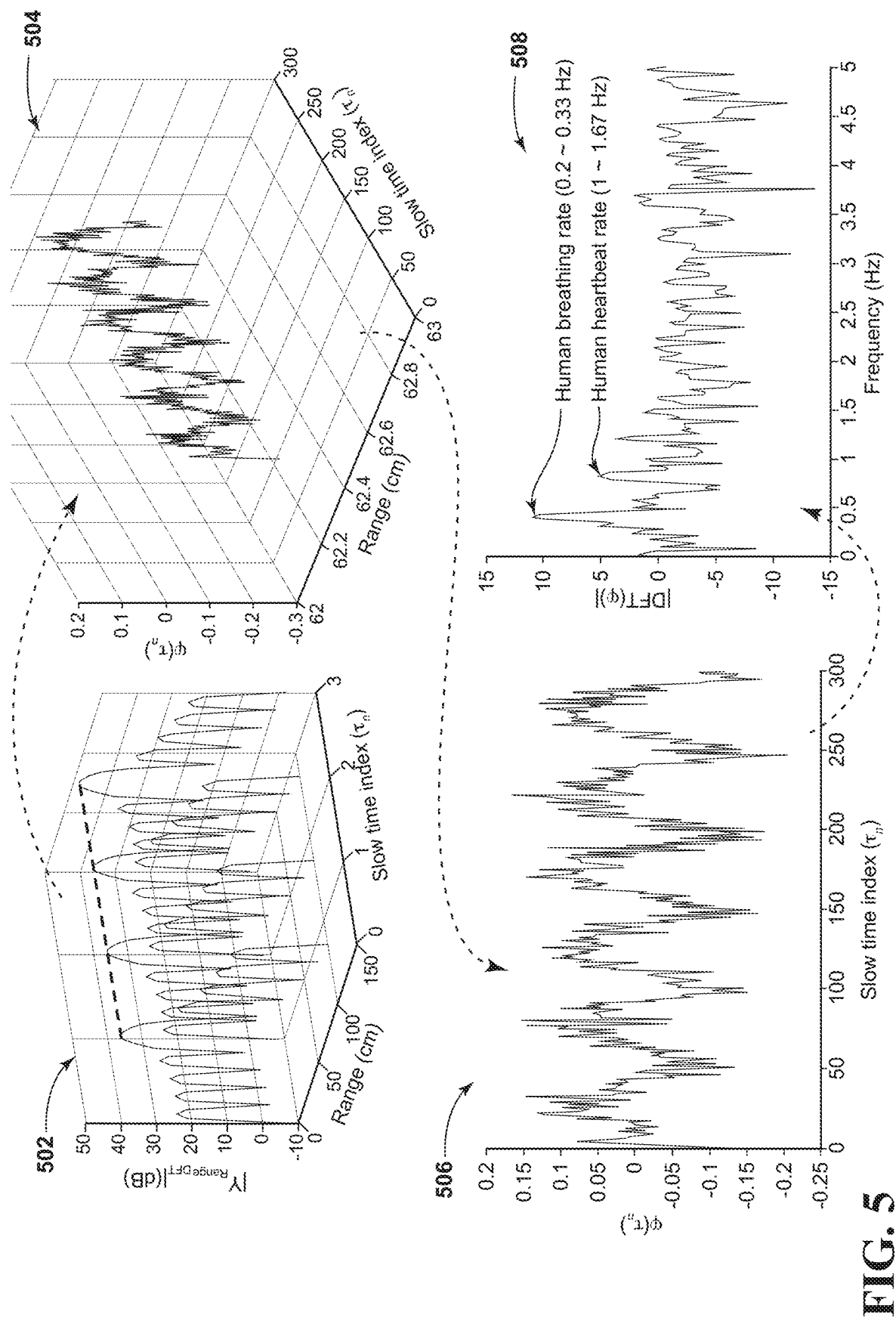
FIG. 5 is a series of charts illustrating data processing for extracting or observing human vital signs from a series of radar echoes according to some aspects of the disclosure.

Referring now to FIG. 5, a series of charts conceptually illustrate the extraction of breathing and heartbeat vital signs utilizing an FMCW radar according to some aspects of this disclosure. For example, a first chart 502, shown at the left, illustrates the received power of the reflected signal $|Y_{Range_{DFT}}|$ as a function of the range or distance between the electronic device and the target object. Several realizations of these reflected samples are shown, illustrated in the dimension indexed by the slow time index m.

As seen in the first chart 502, the peak received power of Y occurs at the same range or distance in each sample across the time index τ. Accordingly, the relatively low-resolution range measurement using the peak power of the DFT of the beat signal, which is conventionally utilized with FMCW radar measurements, may not provide the vital signs information desired to determine whether the target object is a human or not.

In the second chart 504, the phase φ of the DFT of the beat signal at the peaks of the measurements shown in chart 502 is plotted. That is, chart 504 shows the phase φ of the beat signal where it has peak energy, as a function of the range or distance between the electronic device and the target object is shown. As in chart 502, here in chart 504, several realizations of these reflected samples are shown, illustrated in the dimension indexed by the slow time index m. Although, while the first chart 502 only showed four realizations, the second chart 504 is extended in the time dimension to show 300 realizations.

The third chart 506 removes the range dimension and maps the data from the second chart 504 to two dimensions, showing the phase φ as a function of the slow index time m. In the illustrated example, all data points in the second chart 504 fall within the same range bin, as a result of any fluctuations in the peak received power of the reflected signal being small enough not to vary from sample to sample. However, in other examples, not all data points will necessarily fall within the same range bin. That is, the target object may be moving relative to the detector; the range may be at or close to a threshold between two range bins; etc. In an aspect of this disclosure, the third chart 506 may include the phase φ as a function of the slow index time m only for samples that fall within the same range bin. That is, if a set of samples are determined to fall within different range bins, a comparison between phases of those samples may be less meaningful. As seen here, although all data points may correspond to the same range bin as determined according to the peak energy measurement, there are generally periodic fluctuations in the phase φ. The fourth chart 508 shows the DFT of the phase φ, showing the amplitude of the phase φ as a function of frequency. Here, the frequency is determined by a conversion based on foreknowledge of the sampling rate corresponding to the slow time index $\tau_n$.

As seen in the fourth chart 508, a clear peak is seen at approximately 0.2 Hz to 0.33 Hz, which is generally the range of a person's breathing rate. Thus, this data can be utilized to show that the target object being measured is a human, as it causes phase changes at a frequency corresponding to a human vital sign, namely, the breath rate. In addition, another clear peak is seen at approximately 1 Hz to 1.67 Hz, which is generally the range of a person's heart rate. In a further aspect of this disclosure, to provide improved sensitivity for heart rate detection, the change (Δ) in the phase φ in consecutive samples may be detected. Essentially, a difference between the values in consecutive samples is a discrete-time analogue to a time derivative of a continuous function. Thus, by computing the difference between consecutive samples, small changes in the phase that occur at the frequency corresponding to a human heart beat can be reliably detected. Moreover, computing this difference can help to attenuate the relatively slow-frequency variations in the phase measurements caused by breathing, which might otherwise mask the relatively weak heart rate signal.

Another technique that certain examples may utilize to improve the resolution of the spectral estimation of the extracted phase signal, may include the use of one or more 'super-resolution' techniques. For example, multiple signal classification (MUSIC) and estimation of signal parameters using rotational invariance (ESPRIT) are spectral estimation techniques known to those of ordinary skill in the art. By virtue of such techniques, peaks in the extracted phase signal at frequencies associated with vital signs such as breathing or a heart beat may be more reliably determined.

Thus, this data can be utilized to show that the target object being measured is a human, as it causes phase changes at a frequency corresponding to another human vital sign, namely, the heart rate.

In other words, even if the identified range bin corresponding to the estimated distance remains the same across successive captures due to a static target object, the phase may nevertheless change following a pattern that has frequency components corresponding to human vital signs.

If the frequency that the electronic device utilizes for an FMCW radar is 30 GHz, for example, then the wavelength λ=1 cm. At this wavelength, if the displacement variation ΔR=5 mm, then the phase rotation at each breath is π radians. Given that a person's chest movement when breathing can be larger than 5 mm, it becomes necessary to ensure that the sampling rate is sufficiently high to avoid aliasing. For example, the sampling rate of radar pulses may be at least double a person's highest predicted breathing rate. In one example, for high-resolution target object measurement to construct the discrete time phase evolution of the echo signal, a sampling rate of 20 Hz may be utilized.

Figure 6:
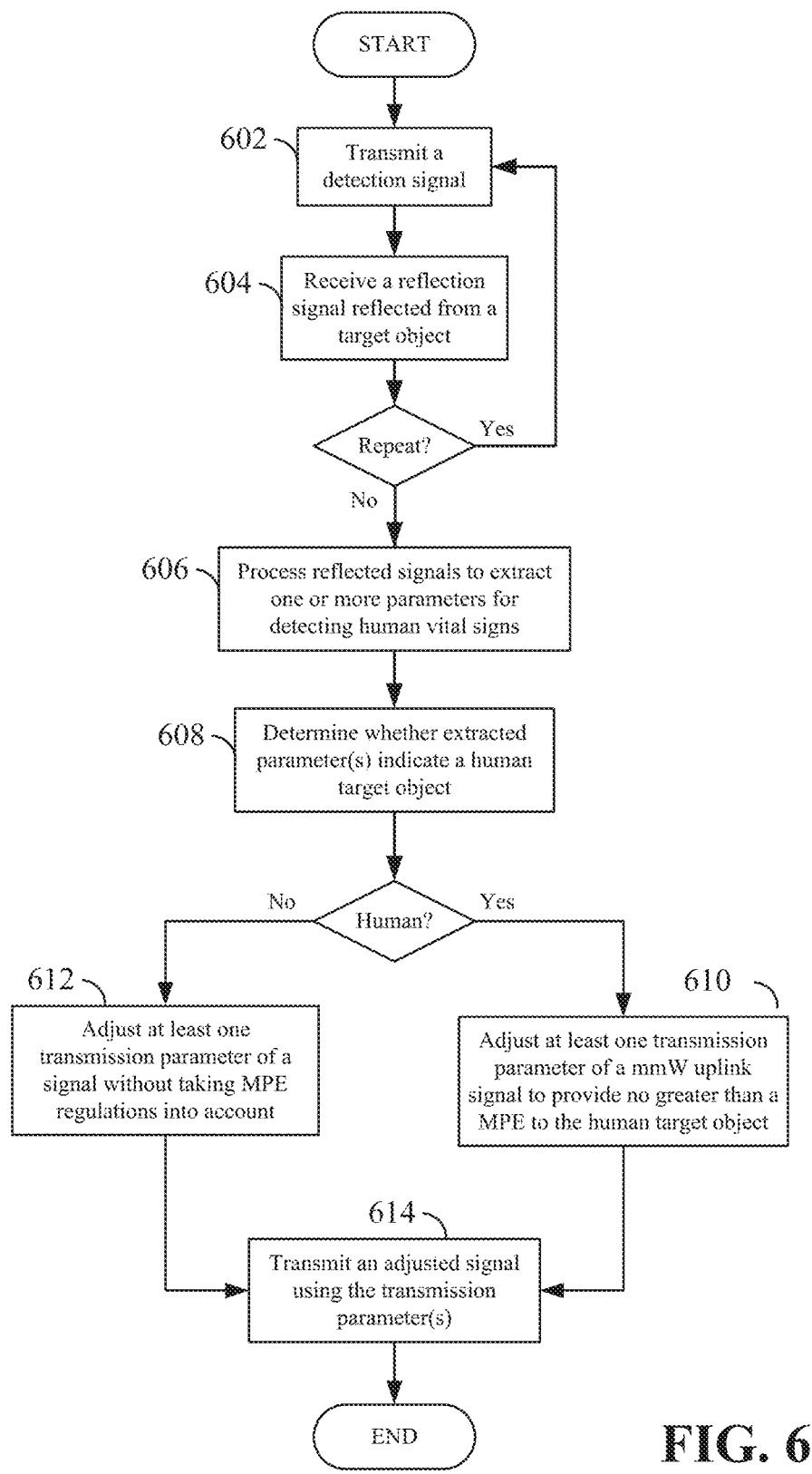
FIG. 6 is a flow chart illustrating an exemplary process for utilizing a vital signs detector to control one or more transmission parameters according to some aspects of the disclosure.

FIG. 6 is a flow chart illustrating an exemplary process for moderating a transmission to reduce exposure to human targets according to some aspects of the present disclosure. Though a human may be used as an example, any living animal may be the basis of adjusting transmission power. As described below, some or all illustrated features may be omitted in a particular implementation within the scope of the present disclosure, and some illustrated features may not be required for implementation of all embodiments. In some examples, the process of FIG. 6 may be carried out by the electronic device 102 illustrated in FIGS. 1 and/or 2. In some examples, the process of FIG. 6 may be carried out by the various components of the electronic device, including but not limited to a transceiver 120 and processor or DSP circuitry 128 as illustrated in FIGS. 3 and/or 4. In some examples, the process of FIG. 6 may be carried out by any suitable apparatus or means for carrying out the functions or algorithm described below.

At block 602, an electronic device 102 may transmit a detection signal. For example, a transceiver 120 may utilize one or more antennas, such as a transmit antenna 210-1 to transmit a pulse, an FMCW signal, a multi-tone signal, or any other suitable signal for radar-based proximity detection.

At block 604, the electronic device 102 may receive a reflection signal reflected from a target object. For example, the transceiver 120 may utilize one or more antennas, such as a receive antenna 210-2 to receive the reflection signal. This process at blocks 602 and 604 may be repeated any suitable number of times, with samples of the reflection signals being taken at any suitable sampling rate. As described above, some examples may utilize a sampling rate of 20 Hz.

At block 606, the electronic device 102 may process the reflected signals to extract the parameters for determining whether the reflected signals include human vital signs. For example, as described above, the electronic device 102 may combine the transmitted signal with the reflected signal to obtain a beat signal, and may then transform the beat signal to the frequency domain, e.g., by calculating the DFT of the beat signal. The electronic device 102 may then extract the phase of the beat signal, taken at the peak power of the DFT of the beat signal at each realization. The electronic device 102 may then calculate the DFT of this extracted phase information (based on the sampling rate of the sequence of realizations) to obtain a frequency-domain data set of the phase samples, as described above and illustrated in chart 508 in FIG. 5.

At block 608, the electronic device 102 may determine whether the extracted parameter(s) indicate a human target object. For example, the electronic device 102 may determine whether the frequency-domain representation of the phase information includes one or more peaks at greater than a threshold magnitude within frequency ranges corresponding to known human vital signs. For example, if greater than a threshold magnitude peak exists in the range of about 0.2 Hz to 0.33 Hz, then the data may be said to represent periodic micromovements caused by human breathing. Similarly, if greater than a threshold magnitude peak exists in the range of about 1 Hz to 1.67 Hz, then the data may be said to represent periodic micromovements caused by a human heart beat. The thresholds used by the electronic device 102 within the desired frequency ranges may take any suitable value, and in some implementations may be experimentally determined based on testing various people's vital signs in various conditions, at various angles, and on various body parts that may exhibit different levels of micromovements corresponding to the same vital signs.

Different implementations may look for these thresholds for any suitable number of one or more frequency ranges, corresponding to any suitable number of one or more human vital signs. For example, an electronic device 102 may determine that the target object is a human if it detects breathing, a heart beat, or both. If one or more human vital signs are detected, then at block 610 the electronic device 102 may adjust at least one transmission parameter of a transmission signal, such as a mmW uplink signal, to provide no greater than a maximum permissible exposure (MPE) of the mmW signal to the human target object. For example, the electronic device 102 may adjust at least one of a power level of the uplink signal, a beam steering angle of the uplink signal, a frequency of the uplink signal, a selected antenna of the uplink signal, a communication protocol of the uplink signal, or a combination of the above, such that the power of the uplink signal at the human target object is no greater than the MPE regulatory requirements.

On the other hand, if the electronic device 102 determines that human vital signs are not detected, then at block 612 the electronic device 102 may adjust at least one transmission parameter of a transmission signal without taking MPE regulations into account. For example, the electronic device may adjust the transmission parameter(s) in such a way that the power of the transmitted signal may exceed an MPE level at the non-human target object.

At block 614, the electronic device 102 may transmit an adjusted signal using the adjusted transmission parameter, as described above.

By utilizing this algorithm, an electronic device can reliably discriminate between human and non-human target objects by monitoring for vital signs utilizing a radar-based proximity detector. In this way, an electronic device can classify humans even when they are stationary, such as when they are passed out or in deep sleep. In some examples, the algorithm may be utilized by conventional FMCW radar-based proximity detector circuits that already exist on the market today. That is, information from such an FMCW radar-based proximity detector can be taken, and a set of consecutive radar echoes, captures, or realizations may be stored in memory. These stored realizations may then be post-processed to extract the phase variations over time by utilizing an additional DFT.

Figure 7:
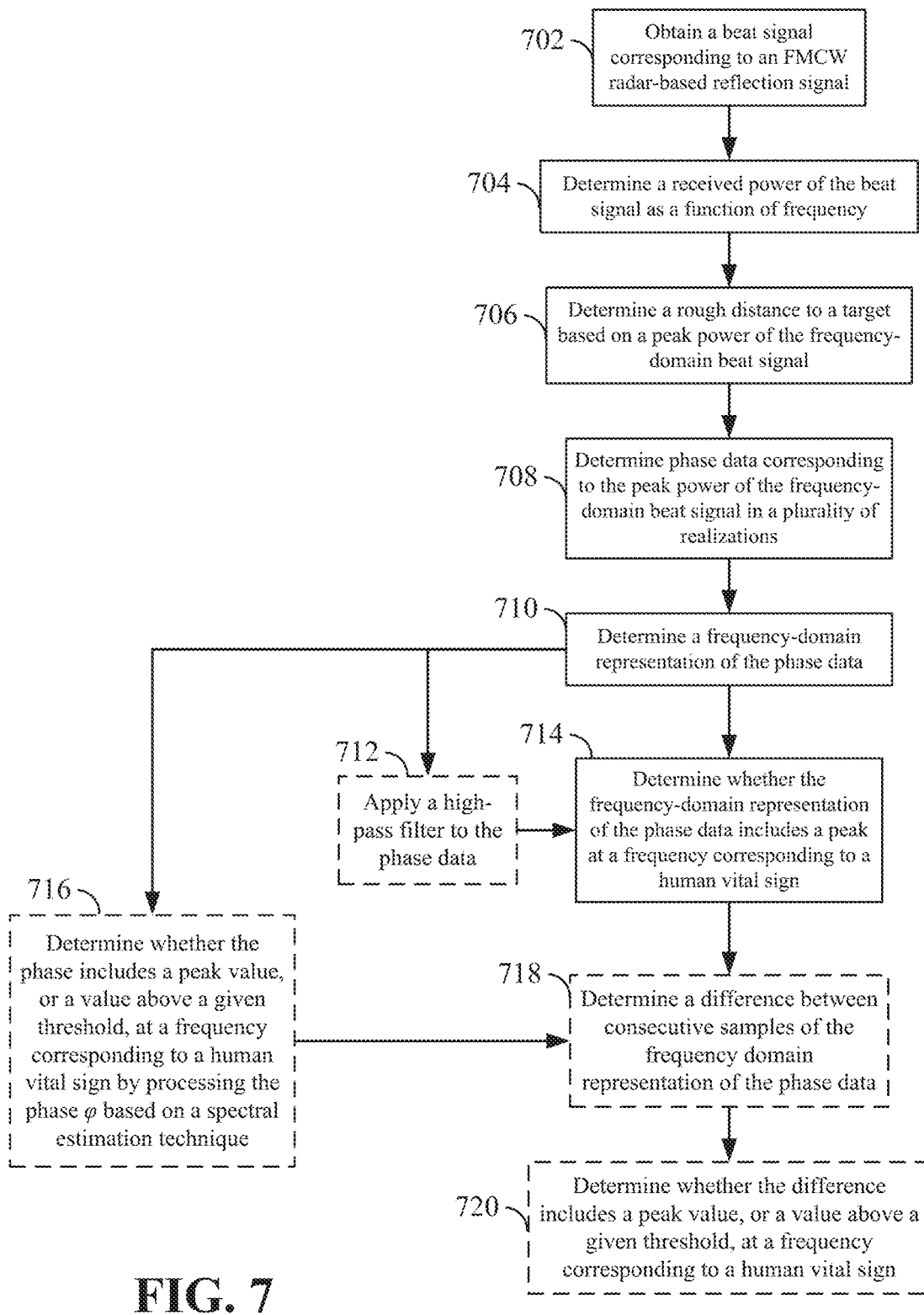
FIG. 7 is a flow chart illustrating a further exemplary process for utilizing a vital signs detector to determine one or more vital signs corresponding to a human vital sign according to some aspects of the disclosure.

FIG. 7 is a flow chart illustrating an exemplary process for detecting, measuring, or characterizing a target according to some aspects of the present disclosure. As described below, some or all illustrated features may be omitted in a particular implementation within the scope of the present disclosure, and some illustrated features may not be required for implementation of all embodiments. In some examples, the process of FIG. 7 may be carried out by the electronic device 102 illustrated in FIGS. 1 and/or 2. In some examples, the process of FIG. 7 may be carried out by the various components of the electronic device, including but not limited to a transceiver 120 and processor or DSP circuitry 128 as illustrated in FIG. 3 or 4. In some examples, the process of FIG. 7 may be carried out by any suitable apparatus or means for carrying out the functions or algorithm described below.

At block 702, an electronic device 102 may obtain a beat signal y(t), e.g., corresponding to an FMCW radar-based reflection signal, as described above:

$$y(t) = A_{Rx} e^{j[2\pi f_b t + \varphi(\tau)]}$$

For example, a transceiver 120 may transmit a detection signal and/or receive a reflection signal, and the processor/DSP circuitry 128 may combine the transmitted signal with the reflected signal to obtain the beat signal y(t).

At block 704, the electronic device 102 may determine a received power $|Y_{Freq}|$ of the beat signal y(t) as a function of frequency. For example, the processor/DSP circuitry 128 may transform the beat signal y(t) to the frequency domain, e.g., by calculating a DFT of the beat signal.

$$Y_{Freq} = DFT[y(t)]$$

At block 706, the electronic device 102 may determine a rough distance R to a target based on a peak power of the frequency-domain beat signal $Y_{Freq}$. For example, the processor/DSP circuitry 128 may determine a peak or maximum value of the received power of the reflected signal, and determine a frequency $f_b$ corresponding to this peak. As described above, the rough distance R can be obtained from this frequency based on the equation:

$$R = \frac{f_b c}{2K}$$

At block 708, the electronic device 102 may determine a phase φ corresponding to the peak power of the frequency-domain beat signal in a plurality of realizations. Here, as described above, the phase φ determined here may correspond to a set of realizations that each have a rough distance R that falls in the same range bin. In other examples, the phase φ determined here may correspond to a set of realizations that each have a rough distance R that falls within a threshold distance of a suitable given distance.

$$\varphi(\tau) = \frac{4\pi \Delta R(\tau)}{\lambda}$$

At block 710, the electronic device 102 may determine a frequency domain representation of the phase data φ. For example, the processor/DSP circuitry 128 may calculate the discrete Fourier transform DFT[φ(τ)], based on the sampling rate τ.

At optional block 712, the electronic device 102 may apply a high-pass filter to the phase data to attenuate a lower-frequency signal associated with breathing, for enhancing a higher-frequency signal associated with a heart rate. For example, the processor/DSP circuitry 128 may apply any suitable low-pass IIR or FIR filter to the phase data φ.

At block 714, the electronic device 102 may determine whether the frequency-domain representation of the phase data φ includes a peak at a frequency corresponding to a human vital sign, such as a breathing rate, a heart rate, and/or a condition or data corresponding to human organs. For example, the processor/DSP circuitry 128 may determine one or more local or global maxima of the frequency-domain representation of the phase data φ, and/or one or more peaks that reach above a suitable threshold value. The processor/DSP circuitry 128 may then determine the frequency corresponding to the determined peak or peaks, and determine whether the frequency lies within a range corresponding to a projected heart rate, and/or within a range corresponding to a projected breathing rate.

At optional block 718, the electronic device 102 may determine a difference Δ between consecutive samples of the frequency domain representation of the phase φ. Similar to a time derivative of a continuous-time function, a difference Δ of a discrete-time function such as DFT[φ(τ)] can provide a rate of change of the frequency-domain phase data.

And at optional block 720, the electronic device 102 may determine whether the difference Δ includes a peak value, or a value above a given threshold, at a frequency corresponding to a human vital sign (e.g., within a range corresponding to a projected heart rate, and/or within a range corresponding to a projected breathing rate).

According to various aspects, the peak(s) determined at block 714 and/or 720 may provide human vital sign information such as a heart rate and/or a breathing rate, which can be utilized for any suitable purpose.

In another example, after the electronic device 102 determines the frequency-domain representation of the phase data at block 710, the process may proceed to block 716. Here, the electronic device 102 may utilize the processor/DSP 128 to determine whether the phase φ includes a peak value, or a value above a given threshold, at a frequency corresponding to a human vital sign by processing the phase φ based on a spectral estimation technique such as, e.g., Multiple Signal Classification (MUSIC) or Estimation of Signal Parameters using Rotational Invariance (ESPRIT). In this example, the process may then optionally proceed to block 718 and continue as described above.

Although the above description has primarily focused on an example where human vital signs detection can be utilized by a wireless communication device for MPE compliance, the present disclosure is not limited to this field. That is, the use of a radar-based human vital signs detector can be employed in a wide variety of applications beyond this example. Only some examples are described below.

For example, a radar-based human vital signs detector can be utilized in the medical field for heart rate monitoring. In this way, the heart rate of the elderly or of infants can be closely monitored with a simple device in their proximity. Thus, any anomalous heart behavior might be detected in real time, improving treatment and care. In another example, a radar-based human vital signs detector can be utilized for monitoring sleep patterns. For example, the duration of sleeping phases, such as deep sleep, light sleep, REM sleep, etc., can be identified by corresponding breathing patterns and changes in heart rate. Therefore, such a vital signs detector can be utilized to analyze the quality of a person's sleep. In still another example, a radar-based human vital signs detector can be utilized for a variety of functions in a smart home or connected home. Based on the detection of a person's vital signs, as well as their location, parameters in such a connected home can be controlled, such as controlling the air conditioning or heating according to whether humans are detected, and in which part of the room they are detected. Similarly, stereo sound systems can identify where a listener is located, to optimize the acoustic environment.

Figure 8:
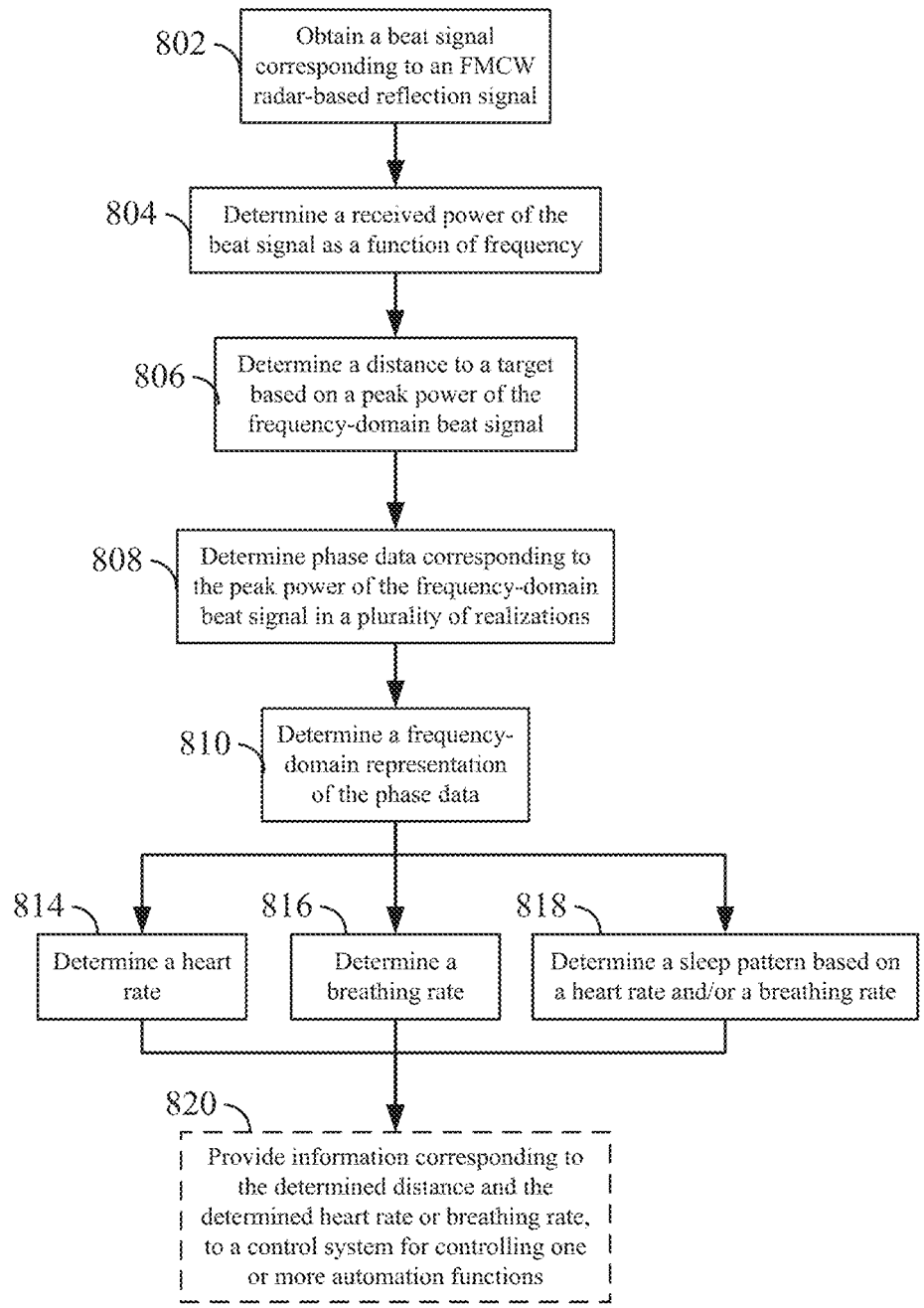
FIG. 8 is a flow chart illustrating a further exemplary process for utilizing a vital signs detector to determine one or more vital signs according to some aspects of the disclosure.

FIG. 8 is a flow chart illustrating an exemplary process for detecting, measuring, or characterizing a target according to further aspects of the present disclosure. As described below, some or all illustrated features may be omitted in a particular implementation within the scope of the present disclosure, and some illustrated features may not be required for implementation of all embodiments. In some examples, the process of FIG. 8 may be carried out by the electronic device 102 illustrated in FIGS. 1 and/or 2. In some examples, the process of FIG. 8 may be carried out by the various components of the electronic device, including but not limited to a transceiver 120 and processor or DSP circuitry 128 as illustrated in FIG. 3 or 4. In some examples, the process of FIG. 8 may be carried out by any suitable apparatus or means for carrying out the functions or algorithm described below.

At block 802, an electronic device 102 may obtain a beat signal y(t), e.g., corresponding to an FMCW radar-based reflection signal, as described above:

$$y(t) = A_{Rx} e^{j[2\pi f_b t + \varphi(\tau)]}$$

For example, a transceiver 120 may transmit a detection signal and/or receive a reflection signal, and the processor/DSP circuitry 128 may combine the transmitted signal with the reflected signal to obtain the beat signal y(t).

At block 804, the electronic device 102 may determine a received power $|Y_{Freq}|$ of the beat signal y(t) as a function of frequency. For example, the processor/DSP circuitry 128 may transform the beat signal y(t) to the frequency domain, e.g., by calculating a DFT of the beat signal.

$$Y_{Freq} = DFT[y(t)]$$

At block 806, the electronic device 102 may determine a rough distance R to a target based on a peak power of the frequency-domain beat signal $Y_{Freq}$. For example, the processor/DSP circuitry 128 may determine a peak or maximum value of the received power of the reflected signal, and determine a frequency $f_b$ corresponding to this peak. As described above, the rough distance R can be obtained from this frequency based on the equation:

$$R = \frac{f_b c}{2K}$$

At block 808, the electronic device 102 may determine a phase φ corresponding to the peak power of the frequency-domain beat signal in a plurality of realizations. Here, as described above, the phase φ determined here may correspond to a set of realizations that each have a rough distance R that falls in the same range bin. In other examples, the phase φ determined here may correspond to a set of realizations that each have a rough distance R that falls within a threshold distance of a suitable given distance.

$$\varphi(\tau) = \frac{4\pi \Delta R(\tau)}{\lambda}$$

At block 810, the electronic device 102 may determine a frequency-domain representation of the phase data co. For example, the processor/DSP circuitry 128 may calculate the discrete Fourier transform DFT[φ(τ)], based on the sampling rate τ.

As described above, various examples implementing different aspects of the present disclosure may provide for determination of a heart rate and/or a breathing rate, dynamically over time. That is, following the determination of the frequency-domain representation of the phase data co, the process of FIG. 8 may proceed to block 814, 816, or 818 in various examples.

At block 814, the electronic device 102 may determine a heart rate based on the frequency-domain representation of the phase data co. For example, the processor/DSP circuitry 128 may identify a peak in the frequency-domain representation of the phase data φ within a threshold distance of a projected heart rate frequency, and may accordingly determine that the frequency of the identified peak corresponds to a measured heart rate.

At block 816, the electronic device 102 may determine a breathing rate based on the frequency-domain representation of the phase data co. For example, the processor/DSP circuitry 128 may identify a peak in the frequency-domain representation of the phase data φ within a threshold distance of a projected breathing rate frequency, and may accordingly determine that the frequency of the identified peak corresponds to a measured breathing rate.

At block 818, the electronic device 102 may determine a sleep pattern based on a heart rate and/or a breathing rate. For example, the processor/DSP circuitry 128 may determine a heart rate and/or a breathing rate as described above in relation to blocks 814 and/or 816. Further, the processor/DSP circuitry 128 may apply the determined heart rate and/or breathing rate to a suitable algorithm associating the respective rate, a change over time of the respective rate, and/or an expected rate with one or more sleep patterns, parameters, or characteristics.

At optional block 820, corresponding to a control system, an automation system, a smart home, or any other suitable processing system, the electronic device 102 may provide information corresponding to the determined distance (e.g., see block 806), the determined heart rate, the determined breathing rate, and/or the determined sleep pattern to a control system. That is, such determined values may be employed as inputs or parameters for a control system for controlling one or more automation functions. Such automation functions may include, but are not limited to smart home functions, climate control functions, audio/video functions, lighting functions, etc.

Further Examples Having a Variety of Features

Example 1: A method, apparatus, and non-transitory computer-readable medium for detecting for vital signs of a target object. An apparatus transmits a plurality of detection signals, and receives a plurality of reflection signals reflected from the target object. The apparatus then processes the plurality of reflection signals to extract one or more parameters for determining whether the plurality of reflection signals indicate human vital signs. Based on whether human vital signs are detected at the target object, the apparatus adjusts at least one transmission parameter and transmits an adjusted signal using the transmission parameter.

Example 2: A method, apparatus, and non-transitory computer-readable medium of Example 1, where the transmission parameter is at least one of a power level, a beam steering angle, a frequency, a selected antenna, and/or a communication protocol.

Example 3: A method, apparatus, and non-transitory computer-readable medium of any of Examples 1 to 2, where the human vital signs are at least one of a breathing rate, a heart rate, and/or a condition or data corresponding to human organs.

Example 4: A method, apparatus, and non-transitory computer-readable medium of any of Examples 1 to 3, where, to process the plurality of reflection signals, the apparatus combines the plurality of detection signals with the plurality of reflection signals to obtain a plurality of beat signals corresponding to a sampling rate. The apparatus then determines a received power of a frequency-domain representation of each one of the plurality of beat signals. The apparatus then determines phase data corresponding to a peak power of each one of the frequency-domain representations of the plurality of beat signals. The apparatus then determines a frequency-domain representation of the phase data with respect to the sampling rate.

Example 5: A method, apparatus, and non-transitory computer-readable medium of any of Examples 1 to 4, where the apparatus further determines whether the frequency-domain representation of the phase data includes a peak greater than a threshold magnitude, within a frequency range corresponding to the human vital signs.

Example 6: A method, apparatus, and non-transitory computer-readable medium of any of Examples 1 to 5, where, to process the plurality of reflection signals, the apparatus applies a high-pass filter to the phase data to attenuate a lower-frequency signal associated with breathing, for enhancing a higher-frequency signal associated with a heart rate.

Example 7: A method, apparatus, and non-transitory computer-readable medium of any of Examples 1 to 6, where, to process the plurality of reflection signals, the apparatus calculates a difference between values of the frequency-domain representation of the phase data in consecutive samples and determines whether the difference includes a peak greater than a threshold magnitude, within a frequency range corresponding to the human vital signs.

Example 8: A method, apparatus, and non-transitory computer-readable medium of any of Examples 1 to 7, where the adjusted signal is a millimeter-wave signal. Here, when the apparatus adjusts at least one transmission parameter, the apparatus configures the adjusted signal to provide no greater than a maximum permissible exposure of the millimeter-wave signal to the human target object.

Example 9: A method, apparatus, and non-transitory computer-readable medium of any of Examples 1 to 8 where, to process the plurality of reflection signals, the apparatus utilizes at least one of multiple signal classification (MUSIC) or estimation of signal parameters using rotational invariance (ESPRIT) for spectral estimation.

Example 10: A method, apparatus, and non-transitory computer-readable medium for detecting for vital signs of a target object. An apparatus obtains a beat signal corresponding to a frequency-modulated continuous wave (FMCW) radar-based reflection signal reflected from a target object, corresponding to a sampling rate. The apparatus then determines a distance to the target object based on a peak power of a frequency-domain representation of the beat signal. The apparatus then determines phase data corresponding to the peak power of the frequency-domain representation of the beat signal. Further, the apparatus then determines a frequency-domain representation of the phase data based on the sampling rate and determines the vital signs of the target object based on the frequency-domain representation of the phase data.

Example 11: A method, apparatus, and non-transitory computer-readable medium of Example 10, where the vital signs of the target object include at least one of a heart rate, a breathing rate, and/or a sleep pattern.

Example 12: A method, apparatus, and non-transitory computer-readable medium of any of Examples 10 to 11, where the apparatus further provides information corresponding to the determined distance and the determined vital signs to a control system for controlling one or more automation functions.

Within the present disclosure, the word "exemplary" is used to mean "serving as an example, instance, or illustration." Any implementation or aspect described herein as "exemplary" is not necessarily to be construed as preferred or advantageous over other aspects of the disclosure. Likewise, the term "aspects" does not require that all aspects of the disclosure include the discussed feature, advantage or mode of operation. The term "coupled" is used herein to refer to the direct or indirect coupling between two objects. For example, if object A physically touches object B, and object B touches object C, then objects A and C may still be considered coupled to one another—even if they do not directly physically touch each other. For instance, a first object may be coupled to a second object even though the first object is never directly physically in contact with the second object. The terms "circuit" and "circuitry" are used broadly, and intended to include both hardware implementations of electrical devices and conductors that, when connected and configured, enable the performance of the functions described in the present disclosure, without limitation as to the type of electronic circuits, as well as software implementations of information and instructions that, when executed by a processor, enable the performance of the functions described in the present disclosure.

One or more of the components, steps, features and/or functions illustrated in FIGS. 1-8 may be rearranged and/or combined into a single component, step, feature or function or embodied in several components, steps, or functions. Additional elements, components, steps, and/or functions may also be added without departing from novel features disclosed herein. The apparatus, devices, and/or components illustrated in FIGS. 1-8 may be configured to perform one or more of the methods, features, or steps described herein. The novel algorithms described herein may also be efficiently implemented in software and/or embedded in hardware.

It is to be understood that the specific order or hierarchy of steps in the methods disclosed is an illustration of exemplary processes. Based upon design preferences, it is understood that the specific order or hierarchy of steps in the methods may be rearranged. The accompanying method claims present elements of the various steps in a sample order, and are not meant to be limited to the specific order or hierarchy presented unless specifically recited therein.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but are to be accorded the full scope consistent with the language of the claims, wherein reference to an element in the singular is not intended to mean "one and only one" unless specifically so stated, but rather "one or more." Unless specifically stated otherwise, the term "some" refers to one or more. A phrase referring to "at least one of" a list of items refers to any combination of those items, including single members. As an example, "at least one of: a, b, or c" is intended to cover: a; b; c; a and b; a and c; b and c; and a, b and c. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112(f) unless the element is expressly recited using the phrase "means for" or, in the case of a method claim, the element is recited using the phrase "step for."

What is claimed is:

1. A method of wireless communication, comprising:
transmitting a first sequence of detection signals;
receiving a second sequence of reflection signals reflected from a target object;
generating a third sequence of beat signals based on the first sequence of detection signals and the second sequence of reflection signals;
determining whether a time variation in a phase of the third sequence of beat signals indicates human vital signs corresponding to at least one of a breathing rate or a heart rate at the target object, wherein determining whether the time variation in the phase of the third sequence of beat signals indicates the human vital signs comprises:
  determining a received power of a frequency-domain representation of each beat signal of the third sequence of beat signals;
  determining phase data corresponding to a peak power of each one of the frequency-domain representations of the third sequence of beat signals;
  determining a frequency-domain representation of the phase data; and
  determining whether a magnitude of a difference between values of the frequency-domain representation of the phase data in consecutive beat signals is: greater than a threshold magnitude, and within a frequency range corresponding to the human vital signs;
adjusting at least one transmission parameter based on whether the time variation in the phase of the third sequence of beat signals indicates the human vital signs at the target object; and
transmitting an adjusted signal using the transmission parameter.

2. The method of claim 1, wherein the transmission parameter comprises at least one of a power level, a beam steering angle, a frequency, a selected antenna, or a communication protocol.

3. The method of claim 1, wherein determining whether the time variation in the phase of the third sequence of beat signals indicates the human vital signs comprises:
applying, for enhancing a higher-frequency signal associated with the heart rate, a high-pass filter to the phase data to attenuate a lower-frequency signal associated with breathing.

4. The method of claim 1, wherein the adjusted signal comprises a millimeter-wave signal, and wherein adjusting the at least one transmission parameter comprises:
configuring the adjusted signal to provide no greater than a maximum permissible exposure of the millimeter-wave signal when the time variation in the phase of the third sequence of beat signals indicates the human vital signs.

5. The method of claim 1, wherein determining whether the time variation in the phase of the third sequence of beat signals indicates the human vital signs at the target object comprises utilizing at least one of multiple signal classification (MUSIC) or estimation of signal parameters using rotational invariance (ESPRIT) for spectral estimation.

6. An electronic device for wireless communication, the electronic device comprising:
a processor; and
a transceiver communicatively coupled to the processor, wherein the processor is configured to:
  cause transmission, via the transceiver, of a first sequence of detection signals;
  receive, via the transceiver, a second sequence of reflection signals reflected from a target object;
  generate a third sequence of beat signals based on the first sequence of detection signals and the second sequence of reflection signals;
  determine whether a time variation in a phase of the third sequence of beat signals indicates human vital signs corresponding to at least one of a breathing rate or a heart rate at the target object, wherein to determine whether the time variation in the phase of the third sequence of beat signals indicates the human vital signs at the target object, the processor is configured to:
    determine a received power of a frequency-domain representation of each beat signal of the third sequence of beat signals;
    determine phase data corresponding to a peak power of each one of the frequency-domain representations of the third sequence of beat signals;
    determine a frequency-domain representation of the phase data; and
    determine whether a magnitude of a difference between values of the frequency-domain representation of the phase data in consecutive beat signals is: greater than a threshold magnitude, and within a frequency range corresponding to the human vital signs;
  adjust at least one transmission parameter based on whether the time variation in the phase of the third sequence of beat signals indicates the human vital signs at the target object; and
  cause transmission, via the transceiver, of an adjusted signal, using the transmission parameter.

7. The electronic device of claim 6, wherein the transmission parameter comprises at least one of a power level, a beam steering angle, a frequency, a selected antenna, or a communication protocol.

8. The electronic device of claim 6, wherein to determine whether the time variation in the phase of the third sequence of beat signals indicates the human vital signs at the target object, the processor is further configured to:
apply, for enhancing a higher-frequency signal associated with the heart rate, a high-pass filter to the phase data to attenuate a lower-frequency signal associated with breathing.

9. The electronic device of claim 6, wherein the adjusted signal comprises a millimeter-wave signal, and
wherein, to adjust the at least one transmission parameter, the processor is further configured to:
  configure the adjusted signal to provide no greater than a maximum permissible exposure of the millimeter-wave signal when the time variation in the phase of the third sequence of beat signals indicates the human vital signs.

10. The electronic device of claim 6, wherein to determine whether the time variation in the phase of the third sequence of beat signals indicates the human vital signs at the target object, the processor is configured to utilize at least one of multiple signal classification (MUSIC) or estimation of signal parameters using rotational invariance (ESPRIT) for spectral estimation.

11. A non-transitory computer-readable medium having computer-executable code stored thereon that, when executed, causes an electronic device to:

transmit a first sequence of detection signals;
receive a second sequence of reflection signals reflected from a target object;
generate a third sequence of beat signals based on the first sequence of detection signals and the second sequence of reflection signals;
determine whether a time variation in a phase of the third sequence of beat signals indicates human vital signs corresponding to at least one of a breathing rate or a heart rate at the target object, wherein to determine whether the time variation in the phase of the third sequence of beat signals indicates human vital signs, the computer-executable code, when executed, causes the electronic device to:
  determine a received power of a frequency-domain representation of each beat signal of the third sequence of beat signals;
  determine phase data corresponding to a peak power of each one of the frequency-domain representations of the third sequence of beat signals;
  determine a frequency-domain representation of the phase data; and
  determine whether a magnitude of a difference between values of the frequency-domain representation of the phase data in consecutive beat signals is: greater than a threshold magnitude, and within a frequency range corresponding to the human vital signs;
adjust at least one transmission parameter based on whether the time variation in the phase of the third sequence of beat signals indicates the human vital signs; and
transmit an adjusted signal using the transmission parameter.

12. The non-transitory computer-readable medium of claim 11, wherein the transmission parameter comprises at least one of a power level, a beam steering angle, a frequency, a selected antenna, or a communication protocol.

13. The non-transitory computer-readable medium of claim 11, wherein to determine whether the time variation in the phase of the third sequence of beat signals indicates the human vital signs at the target object, the computer-executable code further comprises code for causing the electronic device to:
apply, for enhancing a higher-frequency signal associated with the heart rate, a high-pass filter to the phase data to attenuate a lower-frequency signal associated with breathing.

14. The non-transitory computer-readable medium of claim 11, wherein the adjusted signal comprises a millimeter-wave signal, and wherein, to transmit the adjusted signal, the computer-executable code further comprises code for causing the electronic device to:
configure the adjusted signal to provide no greater than a maximum permissible exposure of the millimeter-wave signal when the time variation in the phase of the third sequence of beat signals indicates the human vital signs.

15. The non-transitory computer-readable medium of claim 11, wherein to determine whether the time variation in the phase of the third sequence of beat signals indicates the human vital signs at the target object, the computer-executable code further comprises code for causing the electronic device to utilize at least one of multiple signal classification (MUSIC) or estimation of signal parameters using rotational invariance (ESPRIT) for spectral estimation.

16. An electronic device for wireless communication, the electronic device comprising:

means for transmitting a first sequence of detection signals;
means for receiving a second sequence of reflection signals reflected from a target object;
means for generating a third sequence of beat signals based on the first sequence of detection signals and the second sequence of reflection signals;
means for determining whether a time variation in a phase of the third sequence of beat signals indicates human vital signs corresponding to at least one of a breathing rate or a heart rate at the target object, wherein the means for determining whether a time variation in a phase of the third sequence of beat signals indicates human vital signs comprises:
  means for determining a received power of a frequency-domain representation of each beat signal of the third sequence of beat signals;
  means for determining phase data corresponding to a peak power of each one of the frequency-domain representations of the third sequence of beat signals;
  means for determining a frequency-domain representation of the phase data; and
  means for determining whether a magnitude of a difference between values of the frequency-domain representation of the phase data in consecutive beat signals is: greater than a threshold magnitude, and within a frequency range corresponding to the human vital signs;
means for adjusting at least one transmission parameter based on whether the time variation in the phase of the third sequence of beat signals indicates the human vital signs at the target object; and
means for transmitting an adjusted signal using the transmission parameter.

17. The electronic device of claim 16, wherein the transmission parameter comprises at least one of a power level, a beam steering angle, a frequency, a selected antenna, or a communication protocol.

18. The electronic device of claim 16, wherein the means for determining whether the time variation in the phase of the third sequence of beat signals indicates the human vital signs comprises:
means for applying, for enhancing a higher-frequency signal associated with the heart rate, a high-pass filter to the phase data to attenuate a lower-frequency signal associated with breathing.

19. The electronic device of claim 16, wherein the adjusted signal comprises a millimeter-wave signal, and
wherein the means for adjusting the at least one transmission parameter comprises means for configuring the adjusted signal to provide no greater than a maximum permissible exposure of the millimeter-wave signal when the time variation in the phase of the third sequence of beat signals indicates the human vital signs.

20. The electronic device of claim 16, wherein the means for determining whether the time variation in the phase of the third sequence of beat signals indicates the human vital signs at the target object comprises means for utilizing at least one of multiple signal classification (MUSIC) or estimation of signal parameters using rotational invariance (ESPRIT) for spectral estimation.

21. An electronic device configured for detecting vital signs of a target object, the electronic device comprising:
a processor;
a transceiver communicatively coupled to the processor, wherein the processor is configured to:

obtain a sequence of beat signals, corresponding to a frequency-modulated continuous wave (FMCW) radar-based reflection signal reflected from the target object;

determine a distance to the target object based on a peak power of a frequency-domain representation of the sequence of beat signals;

determine phase data corresponding to the peak power of the frequency-domain representation of the sequence of beat signals;

determine a frequency-domain representation of the phase data; and determine the vital signs of the target object corresponding to at least one of a breathing rate or a heart rate at the target object based on the frequency-domain representation of the phase data, wherein to determine the vital signs of the target object, the processor is configured to:

determine whether a magnitude of a difference between values of the frequency-domain representation of the phase data in consecutive beat signals is: greater than a threshold magnitude, and within a frequency range corresponding to the vital signs.

22. The electronic device of claim 21, wherein the processor is further configured to:

provide information corresponding to the determined distance and the determined vital signs to a control system for controlling one or more automation functions.

23. The electronic device of claim 21, wherein the processor is further configured to:

provide information corresponding to the determined distance.

24. The electronic device of claim 21, wherein the processor is further configured to:

provide information corresponding the determined vital signs.

25. A non-transitory computer-readable medium having computer-executable code stored thereon that, when executed, causes an electronic device to:

obtain a sequence of beat signals corresponding to a frequency-modulated continuous wave (FMCW) radar-based reflection signal reflected from a target object;

determine a distance to the target object based on a peak power of a frequency-domain representation of the sequence of beat signals;

determine phase data corresponding to the peak power of the frequency-domain representation of the sequence of beat signals;

determine a frequency-domain representation of the phase data; and determine vital signs of the target object corresponding to at least one of a breathing rate or a heart rate at the target object based on the frequency-domain representation of the phase data, wherein to determine the vital signs of the target object, the computer-executable code, when executed, causes the electronic device to:

determine whether a magnitude of a difference between values of the frequency-domain representation of the phase data in consecutive beat signals is: greater than a threshold magnitude, and within a frequency range corresponding to the vital signs.

26. The non-transitory computer-readable medium of claim 25, wherein the computer-executable code further comprises code that, when executed, causes the electronic device to:

provide information corresponding to the determined distance and the determined vital signs to a control system for controlling one or more automation functions.

27. The non-transitory computer-readable medium of claim 25, wherein the computer-executable code further comprises code that, when executed, causes the electronic device to:

provide information corresponding to the determined distance to a control system.

28. The non-transitory computer-readable medium of claim 25, wherein the computer-executable code further comprises code that, when executed, causes the electronic device to:

provide information corresponding to the determined vital signs to a control system.

* * * * *